US010463426B2

(12) United States Patent
Chornenky et al.

(10) Patent No.: US 10,463,426 B2
(45) Date of Patent: *Nov. 5, 2019

(54) METHOD FOR TREATING A TUBULAR ANATOMICAL STRUCTURE

(71) Applicant: ANGIODYNAMICS, INC., Latham, NY (US)

(72) Inventors: Victor I Chornenky, Minnetonka, MN (US); Ali Jaafar, Eden Prairie, MN (US)

(73) Assignee: ANGIODYNAMICS, INC., Latham, NY (US)

( * ) Notice: Subject to any disclaimer, the term of this patent is extended or adjusted under 35 U.S.C. 154(b) by 458 days.

This patent is subject to a terminal disclaimer.

(21) Appl. No.: 15/296,501

(22) Filed: Oct. 18, 2016

(65) Prior Publication Data

US 2017/0035501 A1    Feb. 9, 2017

Related U.S. Application Data

(60) Continuation of application No. 14/590,043, filed on Jan. 6, 2015, now Pat. No. 9,480,524, which is a
(Continued)

(51) Int. Cl.
*A61B 18/12* (2006.01)
*A61B 18/14* (2006.01)
(Continued)

(52) U.S. Cl.
CPC .......... *A61B 18/1492* (2013.01); *A61B 18/12* (2013.01); *A61B 18/1206* (2013.01);
(Continued)

(58) Field of Classification Search
None
See application file for complete search history.

(56) References Cited

U.S. PATENT DOCUMENTS 1,653,819 A    12/1927   Ephraim et al.
3,730,238 A     5/1973   Butler
(Continued)

FOREIGN PATENT DOCUMENTS

EP    2488251 A2    8/2012
EP    2593179 A1    5/2013
(Continued)

OTHER PUBLICATIONS

Coates, et al, The electric discharge of the electric eel, *Electrophorus electricus* (Linnaeus), Zoologica: New York Zoological Society, pp. 1-32.
(Continued)

*Primary Examiner* — Daniel W Fowler
(74) *Attorney, Agent, or Firm* — Peter Flora

(57) ABSTRACT

An apparatus and method for treatment of a tubular anatomical structure is disclosed. The method includes using an electrical energy to destroy elongated cells on the tubular anatomical structure. The apparatus may include one or more electrodes for creating an electric field, and a cooling system for carrying heat away from the electrode. The elongated cells can include nerve cells on the tubular anatomical structure.

17 Claims, 5 Drawing Sheets

Related U.S. Application Data continuation of application No. 14/134,109, filed on Dec. 19, 2013, now Pat. No. 8,958,888, which is a continuation of application No. 12/820,955, filed on Jun. 22, 2010, now Pat. No. 8,634,929, which is a continuation of application No. 11/347,965, filed on Feb. 6, 2006, now Pat. No. 7,765,010, which is a division of application No. 10/217,749, filed on Aug. 13, 2002, now Pat. No. 6,994,706.

(60) Provisional application No. 60/325,994, filed on Oct. 1, 2001, provisional application No. 60/311,792, filed on Aug. 13, 2001.

(51) Int. Cl.
*A61N 1/32* (2006.01)
*A61B 18/00* (2006.01)

(52) U.S. Cl.
CPC .... *A61N 1/325* (2013.01); *A61B 2018/00029* (2013.01); *A61B 2018/00285* (2013.01); *A61B 2018/00434* (2013.01); *A61B 2018/00517* (2013.01); *A61B 2018/00547* (2013.01); *A61B 2018/00613* (2013.01); *A61B 2018/00791* (2013.01); *A61B 2018/00875* (2013.01); *A61B 2018/124* (2013.01)

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy, Jr. et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,222,997 A | 6/1993 | Montgomery |
| 5,224,933 A | 7/1993 | Bromander |
| 5,227,730 A | 7/1993 | King et al. |
| 5,233,515 A * | 8/1993 | Cosman ............... A61B 5/042 600/549 |
| 5,242,415 A | 9/1993 | Kantrowitz et al. |
| 5,273,525 A | 12/1993 | Hofmann |
| 5,277,201 A | 1/1994 | Stern |
| 5,279,564 A | 1/1994 | Taylor |
| 5,281,213 A | 1/1994 | Milder et al. |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,417,687 A | 5/1995 | Nardella et al. |
| 5,425,752 A | 6/1995 | Vu'Nguyen |
| 5,439,440 A | 8/1995 | Hofmann |
| 5,439,444 A | 8/1995 | Andersen et al. |
| 5,458,597 A | 10/1995 | Edwards et al. |
| 5,458,625 A | 10/1995 | Kendall |
| 5,462,521 A | 10/1995 | Brucker et al. |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| 5,630,426 A | 5/1997 | Eggers et al. |

(56) References Cited

U.S. PATENT DOCUMENTS

| | | |
|---|---|---|
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,672,174 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,707,332 A | 1/1998 | Weinberger |
| 5,718,246 A | 2/1998 | Vona |
| 5,720,921 A | 2/1998 | Meserol |
| 5,728,143 A | 3/1998 | Gough et al. |
| 5,735,847 A | 4/1998 | Gough et al. |
| 5,752,939 A | 5/1998 | Makoto |
| 5,778,894 A | 7/1998 | Dorogi et al. |
| 5,782,827 A | 7/1998 | Gough et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,810,804 A | 9/1998 | Gough et al. |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,863,290 A | 1/1999 | Gough et al. |
| 5,865,787 A | 2/1999 | Shapland et al. |
| 5,866,756 A | 2/1999 | Giros et al. |
| 5,868,708 A | 2/1999 | Hart et al. |
| 5,873,849 A | 2/1999 | Bernard |
| 5,904,648 A | 5/1999 | Arndt et al. |
| 5,913,855 A | 6/1999 | Gough et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,954,745 A | 9/1999 | Gertler et al. |
| 5,957,919 A | 9/1999 | Laufer |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,012,885 A | 1/2000 | Taylor et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,083,255 A * | 7/2000 | Laufer ................ A61B 18/00 607/101 |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| 6,102,885 A | 8/2000 | Bass |
| 6,106,521 A | 8/2000 | Blewett et al. |
| 6,106,524 A | 8/2000 | Eggers et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,139,545 A | 10/2000 | Utley et al. |
| 6,150,148 A | 11/2000 | Nanda et al. |
| 6,159,163 A | 12/2000 | Strauss et al. |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| 6,233,490 B1 | 5/2001 | Kasevich |
| 6,235,023 B1 | 5/2001 | Lee et al. |
| 6,241,702 B1 | 6/2001 | Lundquist et al. |
| 6,241,725 B1 | 6/2001 | Cosman |
| 6,258,087 B1 * | 7/2001 | Edwards ................ A61B 18/12 600/374 |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,328,735 B1 | 12/2001 | Curley et al. |
| 6,330,478 B1 | 12/2001 | Lee et al. |
| 6,347,247 B1 | 2/2002 | Dev et al. |
| 6,349,233 B1 | 2/2002 | Adams |
| 6,351,674 B2 | 2/2002 | Silverstone |
| 6,387,671 B1 | 5/2002 | Rubinsky et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,443,952 B1 | 9/2002 | Mulier et al. |
| 6,463,331 B1 | 10/2002 | Edwards |
| 6,470,211 B1 | 10/2002 | Ideker et al. |
| 6,478,793 B1 | 11/2002 | Cosman et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,497,704 B2 | 12/2002 | Ein-Gal |
| 6,500,173 B2 | 12/2002 | Underwood et al. |
| 6,503,248 B1 | 1/2003 | Levine |
| 6,506,189 B1 | 1/2003 | Rittman, III et al. |
| 6,514,248 B1 | 2/2003 | Eggers et al. |
| 6,520,183 B2 | 2/2003 | Amar |
| 6,526,320 B2 | 2/2003 | Mitchell |

(56) References Cited

U.S. PATENT DOCUMENTS

| | | | |
|---|---|---|---|
| 6,530,922 B2 | 3/2003 | Cosman et al. |
| 6,533,784 B2 | 3/2003 | Truckai et al. |
| 6,537,976 B1 | 3/2003 | Gupta |
| 6,558,378 B2 | 5/2003 | Sherman et al. |
| 6,562,604 B2 | 5/2003 | Rubinsky et al. |
| 6,575,967 B1 | 6/2003 | Leveen et al. |
| 6,575,969 B1 | 6/2003 | Rittman, III et al. |
| 6,589,161 B2 | 7/2003 | Corcoran |
| 6,589,174 B1 | 7/2003 | Chopra et al. |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | McCormick et al. |
| 6,616,657 B2 | 9/2003 | Simpson et al. |
| 6,627,421 B1 | 9/2003 | Unger et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,682,501 B1 | 1/2004 | Nelson et al. |
| 6,689,096 B1 | 2/2004 | Loubens et al. |
| 6,689,127 B1 | 2/2004 | Gough et al. |
| 6,692,493 B2 | 2/2004 | McGovern et al. |
| 6,694,979 B2 | 2/2004 | Deem et al. |

FOREIGN PATENT DOCUMENTS

| | | | |
|---|---|---|---|
| EP | 2627274 A2 | 8/2013 |
| EP | 2651505 A1 | 10/2013 |
| ES | 2300272 T3 | 6/2008 |
| ES | 2315493 T3 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010511467 A | 4/2010 |
| JP | 2012510332 A | 5/2012 |
| JP | 4252316 B2 | 9/2012 |
| JP | 2012521863 A | 9/2012 |
| KR | 101034682 B1 | 9/2012 |
| WO | WO9104014 A1 | 4/1991 |
| WO | WO9634571 A1 | 11/1996 |
| WO | WO9639531 A1 | 12/1996 |
| WO | WO9810745 A1 | 3/1998 |
| WO | WO9814238 A1 | 4/1998 |
| WO | WO9901076 A1 | 1/1999 |
| WO | WO9904710 A1 | 2/1999 |
| WO | WO0020554 A1 | 4/2000 |
| WO | WO0107583 A1 | 2/2001 |
| WO | WO0107584 A1 | 2/2001 |
| WO | WO0107585 A1 | 2/2001 |
| WO | WO0110319 A1 | 2/2001 |
| WO | WO0148153 A1 | 7/2001 |
| WO | WO0170114 A1 | 9/2001 |
| WO | WO0181533 A1 | 11/2001 |
| WO | WO0200554 A1 | 1/2002 |
| WO | WO02078527 A2 | 10/2002 |
| WO | WO02089686 A1 | 11/2002 |
| WO | WO02100459 A2 | 12/2002 |
| WO | WO03020144 A1 | 3/2003 |
| WO | WO03047684 A2 | 6/2003 |
| WO | WO03099382 A1 | 12/2003 |
| WO | WO2004037341 A2 | 5/2004 |
| WO | WO2004080347 A2 | 5/2004 |
| WO | WO2005065284 A2 | 5/2004 |
| WO | WO2006017666 A2 | 2/2006 |
| WO | WO2006130194 A2 | 12/2006 |
| WO | WO2007067628 A1 | 6/2007 |
| WO | WO2007067937 A2 | 6/2007 |
| WO | WO2007067938 A2 | 6/2007 |
| WO | WO2007067939 A2 | 6/2007 |
| WO | WO2007067940 A2 | 6/2007 |
| WO | WO2007067941 A2 | 6/2007 |
| WO | WO2007067943 A2 | 6/2007 |
| WO | WO2007070361 A2 | 6/2007 |
| WO | WO2007123690 A2 | 11/2007 |
| WO | WO2007137303 A2 | 11/2007 |
| WO | WO2008063195 A1 | 5/2008 |
| WO | WO2008101086 A2 | 8/2008 |
| WO | WO2008101091 A2 | 8/2008 |
| WO | WO2009036468 A1 | 3/2009 |
| WO | WO2009046176 A1 | 4/2009 |
| WO | WO2009134876 A1 | 11/2009 |
| WO | WO2009135070 A1 | 11/2009 |
| WO | WO2009137800 A2 | 11/2009 |
| WO | WO2010064154 A1 | 6/2010 |
| WO | WO2010085765 A2 | 7/2010 |
| WO | WO2010117806 A1 | 10/2010 |
| WO | WO2010118387 A1 | 10/2010 |
| WO | WO2010128373 A1 | 11/2010 |
| WO | WO2010132472 A1 | 11/2010 |
| WO | WO2010151277 A1 | 12/2010 |
| WO | WO2011028937 A1 | 3/2011 |
| WO | WO2011047387 A2 | 4/2011 |
| WO | WO2011062653 A1 | 5/2011 |
| WO | WO2011072221 A1 | 6/2011 |
| WO | WO2011135294 A1 | 11/2011 |
| WO | WO2012006533 A1 | 1/2012 |
| WO | WO2012051433 A2 | 4/2012 |
| WO | WO2012054560 A1 | 4/2012 |
| WO | WO2012054573 A2 | 4/2012 |
| WO | WO2012063266 A2 | 5/2012 |
| WO | WO2012071526 A2 | 5/2012 |
| WO | WO2012088149 A2 | 6/2012 |

OTHER PUBLICATIONS

Lynn, et al, A new method for the generation and use of focused ultrasound in experimental biology, pp. 179-193.

Clark, et al, The Electrical Properties of Resting and Secreting Pancreas, pp. 247-260.

Neumann, Rosenheck, Permeability changes induced by electric impulses in vesicular membranes, J. Membrane Biol., 1972, 10, pp. 279-290.

Crowley, Electrical breakdown of bimolecular lipid membranes as an electromechanical instability, Biophysical Journal, 1973, vol. 13, 711-724.

Zimmermann, et al, Dielectric breakdown of cell membranes, Biophysical Journal, 1974, vol. 14, pp. 881-899.

Organ, Electrophysiologic principles of radiofrequency lesion making, Appl. Neurophysiol., 1976, 39, pp. 69-76.

Kinosita, Jr., Tsong, Hemodialysis of human erythrocytes by a transient electric field, Biochemistry, 1977, vol. 74, No. 5, pp. 1923-1927.

Kinsoita, Jr., Tsong, Formation and resealing of pores of controlled sizes in human erythrocyte membrane, Aug. 1977, vol. 268, pp. 438-441.

Kinosita, Jr., Tsong, Voltage-induced pore formation and hemolysis of human erythrocytes, Biochimica et Biophysica Acta, 1977, pp. 227-242.

Baker, Knight, Calcium-dependent exocytosis in bovine adrenal medullary cells with leaky plasma membranes, Nature, Dec. 1978, vol. 276, pp. 620-622.

Gauger, Bentrup, A study of dielectric membrane breakdown in the Fucus egg, J. Membrane Biol., 1979, 48, pp. 249-264.

Erez, Shitzer, Controlled destruction and temperature distributions in biological tissues subjected to monactive electrocoagulation, Transactions of theASME, Feb. 1980, vol. 102, pp. 42-49.

(56) References Cited

OTHER PUBLICATIONS

Neumann, et al, Gene transfer into mouse lyoma cells by electroporation in high electric fields, The EMBO Journal, 1982, vol. 1, No. 7, pp. 841-845.
Seibert, et al, Clonal variation of MCF-7 breast cancer cells in vitro and in athymic nude mice, Cancer Research, May 1983, 43, pp. 2223-2239.
Brown, Phototherapy of tumors, World J. Surg., 1983, 7, 700-709.
Onik, et al, Ultraonic characteristics of frozen liver, Cryobiology, 1984, 21, pp. 321-328.
Gilbert, et al, The use of ultrsound imaging for monitoring cryosurgery, IEEE Frontiers of Engineering and computing in Health Care, 1984, pp. 107-111.
Onik, et al, Sonographic monitoring of hepatic cryosurgery in an experimental animal model, AJR, May 1985, 144, pp. 1043-1047.
Griffiths, The importance of phase measurement in e lectrical impedance tomography, Phys. Med. Biol., Nov. 1987, vol. 32, No. 11, pp. 1435-1444.
Okino, Mohri, Effects of high-voltage electrical impulse and an anticancer drug on in vivo growing tumors, Jpn. J. Cancer Res., Dec. 1987, 78, pp. 1319-1321.
Kinosita, Jr. et al, Electroporation of cell membrane visualized under a pulsed-laser fluorescence microscope, Biophys. J., Jun. 1988, vol. 53, pp. 1015-1019.
Amasha, et al, Quantitative assessment of impedance tomography for temperature measurements in microwave hyperthermia, Clin. Phys. Physiol. Meas., 1988, vol. 9, Suppl. A, pp. 49-53.
Asmai, et al, Dielectric properties of mouse lymphocytes and erythrocytes, Biochimica et Biophysica Acta, 1989, 1010, pp. 49-55.
Griffiths, Zhang, A dual-frequency electrical impedance tomography system, Phys. Med. Biol., 1989, vol. 34, No. 10, pp. 1465-1476.
Rowland, et al, Transvenous ablation of atrioventricular conduction with a low energy power source, Br Heart J, 1989, 62, pp. 361-366.
Marsazalek, et al, Schwan equation and transmembrane potential induced by alternating electric field, Biophysical Journal, Oct. 1990, vol. 58, pp. 1053-1058.
Tekle, et al, Electroporation by using bipolar oscillating electric field: An improved method for DNA transfection of NIH 3T3 cells, Biochemistry, May 1991, vol. 88, pp. 4230-4234.
Mir, et al, Electrochemotherapy potentiation of antitumour effect of bleomycin by local electric pulses, Eur. J. Cancer, 1991, vol. 27, No. 1, pp. 68-72.
Mir, et al, Electrochemotherapy, a novel antitumor treatment: first clinical trial, Cancerology, 1991, 313, pp. 613-618.
Narayan, Dahiya, Establishment and characterization of a human primay prostatic adenocarcinoma cell line (ND-1_, The Journal of Urology, Nov. 1992, vol. 148, pp. 1600-1604.
Griffiths, et al, Measurement of pharyngeal transit time by electrical impedance tomography, Clin. Phys. Physiol. Meas., 1993, vol. 13, Suppl. A, pp. 197-200.
Rols, et al, Highly efficient transfection of mammalian cells by electric field pulses application to large volumes of cell culture by using a flow system, Eur. J. Biochem., 1992, 205, pp. 115-121.
Brown, et al, Blood flow imaging using electrical impedance tomography, Clin. Phys. Physiol. Meas., 1992, vol. 13, Suppl. A, pp. 175-179.
Foster, et al, Production of prostatic lesions in canines usign transrectally administered high-intensity focused ultrasound, Eur Urol, 1993, pp. 330-336.
Shiina, et al, Percutaneous ethanol injection therapy for hepatocellular carcinoma: Results in 146 patients, AJR, May 1993, 160, pp. 1023-1028.
Salford, et al, A new brain tumour therapy combining bleomycin with in vivo electropermeabilization, Biochemical and Biohysical Research Communications, Jul. 30, 1993, vol. 194, No. pp. 938-943.
Glidewell, NG, The use of magnetic resonance imaging data and the inclusion of anisotropic regions in electrical impedance tomography, ISA, 1993, pp. 251-257.

Gascoyne, et al, Membrane changes accompanying the induced differentiation of Friend murine erythroleukemia cells studied by dielectrophoresis, Biochimca et Biophysica Acta, 1993, 1149, pp. 119-126.
Foster, et al, High-intensity focused ultrsound in the treatment of prostatic disease, Eur Urol, 1993, 23(suppl1), pp. 29-33.
Andreason, Electroporation as a technique for the ransfer of macromolecules into mamalian cell lines, J. Tiss. Cult. Meth., 1993, 15, pp. 56-62.
Weaver, Electroporation: A general phenomenon for manipulating cells and tissues, Journal of Cellular Biochemistry, 1993, 51, pp. 426-435.
Barber, Electrical impedance tomography applied potential tomography, Advances in Biomedical Engineering, 1993, IOS Press, pp. 165-173.
Cook, et al, ACT3: a high-speed, high-precision electrical impedance tomograph, IEEE Transactions on Biomedical Engineering, 1994, vol. 41, No. 8, pp. 713-722.
Alberts, et al, Molecular biology of the Cell, Biocchemical education, 1994, 22(3), pp. 164.
Hughes, et al, An analysis of studies comparing electrical impedance tomography with x-ray videofluoroscopy in the assessment of swallowing, Physiol. Meas. 1994, 15, pp. A199-A209.
Griffiths, Tissue spectroscopy with electrical impedance tomography: Computer simulations, IEEE Transactions on Biomedical Engineering, Saep 1995, vol. 42, No. 9, pp. 948-954.
Gencer, et al, Electrical impedance tomography: Induced-currentimaging achieved with a multiple coil system, IEEE Transactions on Biomedical Engineering, Feb. 1996, vol. 43, No. 2, pp. 139-149.
Weaver, Chizmadzhev, Review Theory of electroporation: a review, Biolectrochemistry and Bioenergetics, 1996, 41, pp. 135-160.
Gimsa, et al, Dielectric spectroscopy of single human erythrocytes at physiological ionic strength: Dispersion of the cytoplasm, Biophysical Journal, Jul. 1996, vol. 71, pp. 495-506.
Sabuncu, et al, Dielectrophoretic separation of mouse melanoma clones, Biomicrofluidics, Jun. 16, 2010, 4, 021101, pp. 1-7.
Garcia, et al, Intracranial nonthermal irreversible electroporation: In vivo analysis, J Membrane Biol, Jul. 29, 2010, 236, pp. 127-136.
Neal, et al, Treatment of breast cancer through the application of irreversible electroporation using a novel minimally invasive single needle electrode, Breat Cancer Res Treat, Aug. 27, 2010, 123, 1, pp. 295-301.
Zhang, et al, MR imaging to assess immediate response to irreversible electroporation for targeted ablation of liver tissues: Preclinical feasibility studies in a rodent model, Radiology, Aug. 2010, vol. 256, No. 2, pp. 424-432.
Neal, et al, A study using irreversible electroporation to treat large, irregular tumors in a canine patient, 32nd Annual International Conference of the IEEE EMBS, IEEE, Aug. 2010, pp. 2747-2750.
Garcia, et al, Non-thermal irreversible electroporation for deep intracranial disorders, 32nd Annual International Conferenece of the IEEE EMBS, IEEE, Aug. 2010, pp. 2747463.
Phillips, et al, Nonthermal irreversible electroporation for tissue decellularization, Journal of Biomedical Engineering, Aug. 16, 2010, vol. 132, 091003, pp. 1-8.
Pech, et al, Irreversible electroporation of renal cell carcinoma: A first-in-man phase I clinical study, Cardiovasc Intervent Radiol, Aug. 15, 2010.
Lee, et al, Irreversible electroporation: A novel image-guided cancer therapy, Gut and Liver, Sep. 2010, vol. 4, Supp. 1, pp. S99-S104.
Hong, et al, Cardiac ablation via electroporation, 31st Annual International Conference of the IEEE EMBS, IEEE, Sep. 2, 2010, pp. 3381-3384.
Dupuy, et al, Irreversible electroporation in a swine lung model, Cardiovasc Intervent Radiol, Dec. 30, 2010, 34, pp. 391-395.
Arena, et al, Theoretical considerations of tissue electropration with high frequency biopolar pulses, IEEEE, pp. 1-7.
Deodhar, et al, Renal tissue ablation with irreversible electroporation: Preliminary results in a porcine model, Technology and Engineering, Urology, 2010, 1-7.
McCarley, Soulen, Percutaneous ablation of hepatic tumors, Seminars in Interventional Radiology, 2010, vol. 27, No. 3, pp. 255-260.

(56) References Cited

OTHER PUBLICATIONS

Neu, Neu, Mechanism of irreversible electroporation in cells: Insight from the models, Irreversible Electroporation: Biomed, pp. 85-122.
Charpentier, et al, Irreversible electroporation of the pancreas in swine: A pilot study, HPB, 2010, 12, pp. 348-351.
Tracy, et al, Irreversible electroporation (IRE): A novel method for renal tissue ablation, BJU International, 107, pp. 1982-1987.
Onik, Rubinsky, Irreversible electroporation: First patient experience focal therapy of prostate cancer, Irreversible Electroporation, Biomed, pp. 235-247.
McWilliams, et al, Image-guided tumor ablation: Emerging technologies and future directions, Seminars in Interventional Radiology, 2010, vol. 27, No. 3, pp. 302-313.
Kurup, Callstrom, Image-guided percutaneous ablation of bone and soft tissue tumors, Seminars in Interventional Radiology, 2010, vol. 27, No. 3, pp. 276-284.
Thomson, Human experience with irreversible electroporation, Irreversible Electroporation, Biomed, 2010, pp. 249-354.
Saldanha, et al, Current tumor ablation technologies: Basic science and device review, Seminars in Interventional Radiology, 2010, vol. 27, No. 3, pp. 247-254.
Dupuy, Shulman, Current status of thermal ablation treatments for lung malignancies, Seminars in Interventional Radiology, 2010, vol. 27, No. 3, pp. 268-275.
Carmi, Georgiades, Combination percutaneous and intraarterial therapy for the treatment of hepatocellular carcinoma: A review, Seminars in Interventional Radiology, 2010, vol. 27, No. 3, pp. 296-301.
Jarm, et al, Antivascular effects of electrochemotherapy: implicatoins in treatment of bleeding metastases, Expert Rev. Anticancer Ther., 2010, 10, 5, pp. 729-746.
Maybody, An overview of image-guided percutaneous ablation of renal tumors, Seminars in Interventional Radiology, 2010, vol. 27, No. 3, pp. 261-267.
Goldberg, Rubinsky, A statistical model for multidimensional irreversible electroporation cell death in tissue, Biomedical Engineering Online, 2010, 9:13, pp. 1-13.
Sano, et al, Towards the creation of decellularized organ constructs using irreversible electroporation and active mechanical perfusion, Biomedical Engineering Online, 2010, 9, 83, pp. 1-16.
Mahmood, Gehl, Optimizing clinical performance and geometrical robustness of a new electrode device for intracranial tumor electroporation, Bioelectrochemistry, Jan. 6, 2011, 81, pp. 10-16.
Garcia, et al, Non-thermal irreversible electroporation (N-TIRE) and adjuvant fractionated radiotherapeutic multimodal therapy for intracranial malignant glioma in a canine patient, Feb. 2011, vol. 10, No. 1, pp. 73-83.
Guo, et al, Irreversible electroporation in the liver: Contrast-enhanced inversion-recovery MR imaging approaches to differentiate reversibly electroporated penumbra from irreversibly electroporated ablation zones, Radiology, Feb. 2011, vol. 258, No. 2, pp. 461-468.
Bower, et al, Irreversible electroporation of the pancreas: Definitive local therapy without systemic effects, Journal of Surgical Oncology, Feb. 28, 2011, 104, pp. 22-28.
Ellis, et al, Nonthermal irreversible electroporation for intracranial surgical applications, J Neurosurg, Mar. 2011, 114, pp. 681-688.
Nesin, et al, Manipulation of cell volume and membrane pore comparision following single cell permeabilization with 60- and 600-ns electric pulses, Biochim Biophys Acta, Mar. 2011, 1808(3), pp. 792-801.
McCall, Nanoknife, liposomal doxorubicin show efficacy against liver cancer, European Congress of Radiology, Mar. 7, 2011, pp. 1-2.
Mahmood, et al, Diffusion-weighted MRI for verification of electroporation-based treatments, J Membrane Biol, Mar. 6, 2011, 240, pp. 131-138.
Deodhar, et al, Irreversible electroporation near the heart: Ventricular arrhythmias can be prevented with ECG synchronization, AJR, Mar. 2011, 196, pp. W330-W335.
Garcia, et al, A parametric study delineating irreversible electroporation from thermal damage based on a minimally invasive intracranial procedure, Biomedical Engineering Online, 2011, 10: 34, pp. 1-21.
Li, et al, The effects of irreversible electroporation (IRE) on nerves, PLoS One, Apr. 14, 2011, vol. 6, Iss. 4, e18831, pp. 1-7.
Neal, et al, Successful treatment of a large soft tissue sarcoma with irreversible electroporaiton, Journal of Clinical Oncology, May 1, 2011, vol. 29, No. 13, pp. e372-e377.
Thomson, et al, Investigation of the safety of irreversible electroporation in humans, J Vasc Intery Radiol, May 2011, 22, pp. 611-621.
Rossmeisl, Jr., et al, Successful treatment of a large soft tissue sarcoma with irreversible electroporation, Journal of Clinical Oncology, May 1, 2011, vol. 29, No. 13, pp. e372-e377.
Daniels, Rubinsky, Temperature modulation of electric fields in biological matter, PLoS One, vol. 6, Iss. 6, e20877, pp. 1-9.
Lion, et al, Poly(I:C) enhances the susceptibility of leukemic cells to NK cell cytotoxicity and phagocytosis by DC, PLoS One, vol. 6, Iss. 6, e20952, pp. 1-10.
Agerholm-Larsen, et al, Preclinical validation of electrochemotherapy as an effective treatment for brain tumors, Cancer Res, Jun. 1, 2011, 71, 11, pp. 3753-3762.
Adeyanju, et al, The improvement of irreversible electroporation therapy using saline-irrigated electrodes: A theoretical study, Technology in Cancer Research and Treatment, Aug. 2011, vol. 10, No. 4, pp. 347-360.
Mulhall, et al, Cancer, pre-cancer and normal oral cells distinguished by dielectrophoresis, Anal Bioanal chem, Aug. 30, 2011, 401, pp. 2455-2463.
Troszak, Rubinsky, Self-powered electroporation using a singularity-induced nano-electroporation configuration, Biochemical and Biophysical Research Communications, Sep. 28, 2011, 414, pp. 419-424.
Arena, et al, High-frequency irreversible electroporation (H-FIRE) for non-thermal ablation without muscle contraction, BioMedical Engineering Online, Nov. 21, 2011, 10: 102, pp. 1-20.
Hijouj, et al, Electroporationo-induced BBB disruption and tissue damage depicted by MRI, Neuro-Oncology, Abstracts from the 16th Annual Scientific Meeting, Nov. 17, 2011, vol. 13, Supp 3, ET-32, p. iii114.
Szot, et al, 3D in vitro bioengineered tumors based on collagen I hydrogels, Biomaterials, Nov. 2011, 32(31), pp. 7905-7912.
Bastista, et al, The use of whole organ decellularization for the generation of a vascularized liver organoid, Hepatology, 2011, vol. 53, No. 2, pp. 604-617.
Sano, et al, Modeling and development fo a low frequency contact-less dielectrophoresis (cDEP) platform to sort cancer cells from dilute whole blood samples, Biosensors and Bioelectronics, 2011, pp. 1-8.
Charpentier, et al, Irreversible electroporation of the liver an dliver hilum in swine, HBP, 2011, 13, pp. 168-173.
Sankaranarayanan, et al, Effect of irreversible electroporation on cell proliferation in fibroblasts, Proc. ESA Annual Meeting on Electrostatics, 2011, pp. 1-8.
Sano, et al, Contactless dielectrophoretic spectroscopy: Examination of the dielectric properties of cells found in blood, Electrophoresis, 2011, 32, pp. 3164-3171.
Chen, et al, Classification of cell types using a microfluidic device for mechanical and electrical measurements on single cells, Lab Chip, 2011, 11, pp. 3174-3181.
Rebersek, Miklavcic, Advantages and disadvantages of different concepts of electroporation pulse generation, Automatika, 2011, 52, 1, pp. 12-19.
Ben-David, et al, Characterization of irreversible electroporaiton ablation in in vivo porcine liver, AJR, Jan. 2012, 198, pp. W62-W68.
Appelbaum, et al, US findings after irreversible electroporation ablation: Radiologic-pathologic correlation, Radiology, Jan. 2012, vol. 262, No. 1, pp. 117-125.
Salmanzadeh, et al, Dielectrophoretic differentiation of mouse ovarian surface epithelial cells, macrophages, and fibroblasts using contactless dielectrophoresis, Biomicrofluidics, Apr. 3, 2012, 6, 024104, pp. 1-13.

(56) References Cited

OTHER PUBLICATIONS

Neal, et al, Experimental characterization and numerical modeling of tissue electrical conductivity during pulsed electric fields for irreversible electroporation treatment planning, IEEE Transactions on Biomedical Engineering, Apr. 2012, vol. 59, No. 4, pp. 1076-1085.

Du Pre, et al, Minimal coronary artery damage by myocardial electroporation ablation, European Society of Cardiology, Europace, May 31, 2012, pp. 1-6.

Wittkampf, et al, Myocradial lesion depth with circular electroporation ablation, Circ Arrhythm Electrophysiol, 2012, 5, pp. 581-586.

Arena, et al, Phase change electrodes for reducing joule heating during irreversible electroporation, Proceedings of the ASME 2012 Summer Bioengineering Conference, Jun. 20, 2012, pp. 1-2.

Garcia, et al, Towards a predictive model of electroporation-based therapies using pre-pulse electrical measurements, 34th Annual International Conference of the IEEE EMBS, Aug. 28, 2012, pp. 2575-2578.

Hjouj, et al, MRI study on reversible and irreversible electroporation induced blood brain barrier disruption, Aug. 10, 2012, PLoS One, vol. 7, 8, e42817, pp. 1-9.

Martin, et al, Irreversible electroporation therapy in the management of locally advanced pancreatic adenocarcinoma, American College of Surgeons, Sep. 2012, vol. 215, No. 3, pp. 361-369.

Weaver, et al, A brief overview of electroporation pulse strength-duration space: A region where additional intracellular effects are expected, Bioelectrochemistry, Oct. 2012, 87, pp. 236-243.

Arena, et al, A three-dimensional in vitro tumor platform for modeling therapeutic irreversible electroporation, Biophysical Journal, Nov. 2012, vol. 103, pp. 2033-2042.

Garcia, et al, 7.0-T magnetic resonance imaging characterization of acute blood-brain-barrier disruption achieved with intracranial irreversible electroporation, PLoS One, vol. 7, 11, pp. 1-8.

Arena, et al, Towards the development of latent heat storage electrodes for electroporation-based therapies, Applied Physics Letters, 2012, 101, 083902, pp. 1-4.

Cannon, et al, Safety and early efficacy of irreversible electroporation for hepatic tumors in proximity to vital structures, Journal of Surgical Oncology, 2012, pp. 1-6.

Bagla, Papadouris, Percutaneous irreversible electroporation of surgically unresectable pancreatic cancer: A case report, J Vasc Intery Radiol, 2012, 23, pp. 142-145.

Phillips, et al, Irreversible electroporation on the small intestine, British Journal of Cancer, 2012, pp. 1-6.

Mahnic-Kalamiza, et al, Educational application for visualization and analysis of electric field strength in multiple electrode electroporation, BMC Medical Education, 2012, 12, 102, pp. 1-13.

Kingham, et al, Ablation of perivascular hepatic malignant tumors with irreversible electroporation, J Am Coll Surg, 2012, 215, pp. 379-387.

Salmanzadeh, et al, Investigating dielectric properties of different stages of syngeneic murine ovarian cancer cells, Biomicrofluidics, Jan. 23, 2013, 7, 011809, pp. 1-12.

Faroja, et al, Irreversible electroporation ablation: Is all the damage non-thermal?, Radiology, Feb. 2013, vol. 266, No. 2, pp. 462-470.

Fong, et al, Modeling ewing sarcoma tumors in vitro with 3D scaffolds, PNAS, Apr. 16, 2013, vol. 110, No. 15, pp. 6500-6505.

Garcia, et al, Position paper concerning the use of Angiodynamics' nanoknife system for treatment of brain gliomas, Virgina Tech—Wake Forest University, May 22, 2013, pp. 1-46.

Salmanzadeh, et al, Sphingolipid metabolites modulate dielectric characteristics of cells in a mouse ovarian cancer progression model, Integr Biol, Jun. 2013, 5, 6, pp. 843-852.

Polak, et al, On the electroporation thresholds of lipid bilayers: Molecular dynamics simulation investigations, J Membrane Biol, Jun. 13, 2013, 246, pp. 843-850.

Jiang, et al, Membrane-targeting approaches for enhanced cancer cell destruction with irreversible electroporation, Annuals of Biomedical Engineering, Aug. 15, 2013.

Bayazitoglu, et al, An overview of nanoparticle assisted laser therapy, International Journal of Heat and Mass Transfer, Sep. 11, 2013, 67, pp. 469-486.

Rossmeisl, Jr., et al, Pathology of non-thermal irreversible electroporation (N-TIRE)-induced ablation of the canine brain, Journal of Veterinary Science, 2013, 14, 4, pp. 433-440.

Lu, et al, Irreversible electroporation: Ready for prime time?, Techniques in Vascular and Interventional Radiology, 2013, 16, pp. 277-286.

Dunki-Jacobs, et al, Evaluation of resistance as a measure of successful tumor ablation during irreversible electroporation of the pancreas, American College of Surgeons, Feb. 2014, vol. 218, No. 2, pp. 179-187.

Son, et al, Basic features of a cell electroporation model: illustrative behavior for tw overy different pulses, J Membrane Biol, Jul. 22, 2014, 247, pp. 1209-1228.

Neal, et al, An "Off-the-Shelf" system for intraprocedural electrical current evaluation and monitoring of irreversible electroporation therapy, Cardiovasc Intervent Radiol, Feb. 27, 2014.

Sano, et al, In-vtro bipolar nano- and microsecond electro-pulse bursts for irreversible electroporation therapies, Bioelectrochemistry, Aug. 4, 2014, 100, pp. 69-79.

Rossmeisl, New treatment modalities for brain tumors in dogs and cats, Vet Clin Small Anim, 2014, 44, pp. 1013-1038.

Chen, et al, Preclinical study of locoregional therapy of hepatocellular carcinoma by bioelectric ablation with microsecond pulsed electric fields (usPEFs), Scientific Reports, Apr. 2015, 5, 9851, pp. 1-10.

Trimmer, et al, Minimally invasive percutaneous treatment of small renal tumors with irreversible electroporation: a single-center experience, J Vasc Interv Radiol, 2015, 26: pp. 1465-1471.

Eppich, et al, Pulsed electric fields for seletion of hematopoietic cells and depletion of tumor cell contaminants, Nature America, Aug. 2000, vol. 18, pp. 882-887.

Mir, Therapeutic perspectives of in vivo cell electropermeabilization, Bioelectrochemistry, 2000, 53, pp. 1-10.

Al-Khadra, et al, The role of electroporation in defibrillation, Circulation Research, Oct. 27, 2000, 87, pp. 797-804.

Miklavcic, et al, A validated model of in vivo electric field distribution in tissues for electrochemotherapy and for DNA electrotransfer for gene therapy, Biochimica et Biophysica Acta, 2000, 1523, pp. 73-83.

Rubinsky, Cryosurgery, Annu. Rev. Biomed. Eng. 2000, 2, pp. 157-187.

Jaroszeski, et al, In vivo gene delivery by electroporation, Advanced Drug Delivery Reviews, 1999, 35, pp. 131-137.

Cowley, Lifestyle Good news for boomers, Newsweek, Dec. 30, 1996.

Sharma, et al, Poloxamer 188 decrease susceptibility of artificial lipid membranes to electroporation, Biophysical Journal, 1996, vol. 71, pp. 3229-3241.

Blad, Baldetorp, Impedance spectra of tumour tissue in comparison with normal tissue; a possible clinical application for electrical impedance tomography, Physiol. Meas., 1996, 17, pp. A105-A115.

Ho, Mittal, Electroporation of cell membranes: a review, Critical Reviews in Biotechnology, 1996, 16(4), pp. 349-362.

Gilbert, et al, Rapid report novel electrode designs for electrochemotherapy, Biochimica et Biophysica Acta, Feb. 11, 1997, 1134, pp. 9-14.

Zlotta, et al, Possible mechanisms fo action of transsurethral needle ablation of the prostate on benign prostatic hyperplasia systems: A neurohistochemical study, Journal of Urology, Mar. 1997, vol. 157, No. 3, pp. 894-899.

Duraiswami et al, Solution of electrical impedance tomography equations using boundary element methods, Boundary Element Technology XII, Apr. 1997, pp. 227-237.

Fox, Nicholls, Sampling conductivity images via MCMC, Auckland University, Auckland, New Zealand.

Niaslund, Transurethral needle ablation of the prostate, Urology, Aug. 1997, vol. 50, No. 2, pp. 167-172.

(56) References Cited

OTHER PUBLICATIONS

Boone, et al, Review imaging with electricity: Report of the European concerted action on impedance tomography, Journal of Medical Engineering & Technology, Nov. 1997, vol. 21, No. 6, pp. 201-232.

Lurquin, Review: Gene transfer by electroporation, Molecular Biotechnology, 1997, vol. 7, pp. 5-31.

Hapala, Breaking the barrier: methods for reversible permeabilization of cellular membranes, Critical Reviews in Biotechnology, 1997, 17(2), pp. 105-122.

Duraiswami, et al, Boundary element techniques for efficient 2-D and 3-D electrical impedance tomography, Chemical Engineering Science, 1997, vol. 52, No. 13, pp. 2185-2196.

Pinero, et al, Apoptotic and necrotic cell death are both induced by electroporation in HL60 human promyeloid leukaemia cells, Apoptosis, 1997, 2, pp. 330-336.

Miklavcic, et al, The importance of electric field distribution for effective in vivo electroporation of tissues, Biophysical Journal, May 1998, vol. 74, pp. 2152-2158.

Issa, et al, Recent Reports: The TUNA procedure for BPH: Review of the technology, Infections in Urology, Jul. 1998.

Lundqvist, et al, Altering the biochemical state of individual cultured cells and organelles with ultramicroelectrodes, Proc. Natl. Acad. Sci. USA, Sep. 1998, Vo. 95, pp. 10356-10360.

Issa, et al, Specialty Surgery: The TUNA procedure for BPH: Basic procedure and clinical results, Infections in Urology, Sep. 1998.

Dev, et al, Sustained local delivery of heparin to the rabbit arterial wall with an electroporation catheter, Catheterization and Cardiovascular Diagnosis, 1998, 45, pp. 337-345.

Duraiswami, et al, Efficient 2D and 3D electrical impedance tomography using dual reciprocity boundary element techniques, Engineering Analysis with Boundary Elements, 1998, 22, pp. 13-31.

Mir, et al, Effective treatment of cutaneous and subcutaneous malignant tumors by electrochemotherapy, 1998, British Journal of Cancer, 77 (12), pp. 2336-2342.

Sersa, et al, Tumor blood flow modifying effect of electrochemotherapy with Bleomycin, Anticancer Research, 1999, 19, pp. 4017-4022.

Thompson, et al, To determine whether the temperature of 2% lignocaine gel affects the initial discomfort which may be associated with its instillation into the male urethra, BJU International, 1999, 84, pp. 1035-1037.

Gumerov, et al, The dipole approximation method and its coupling with the regular boundar yelement method for efficient electrical impedance tomography, BETECH 99.

Yang, et al, Dielectric properties of human luekocyte subpopulations determined by electrorotation as a cell separation criterion, Jun. 1999, vol. 76, pp. 3307-3014.

Huang, Rubinsky, Micro-electroporation: improving the efficiency and understanding of electrical permeabilization of cells, Biomedical Microdevices, 1999, 2:2, pp. 145-150.

Mir, Orlowski, Mechanisms of electrochemotherapy, Advanced Drug Delivery Reviews, 1999, 35, pp. 107-118.

Jaroszeski, et al, In vivo gene delivery by electroporationi, Advanced Drug Delivery Reviews, 1999, 35, pp. 131-137.

Gehl, et al, In vivo electroporation of skeletal muscle: threshold, efficacy and relation to electric field distribution Biochimica et Biophysica Acta, 1999, 1428, pp. 233-240.

Heller, et al, Clinical applications of electrochemotherapy, Advanced Drug Delivery Reviews, 1999, 35, 119-129.

Holder, et al, Low-Frequency System, Assessment and calibration of a low-frequency impedance tomography (EIT), optimized for use in imaging brain function in ambulant human subjects, Annals New York Academy Sciences, pp. 512-519.

Dev, et al, Medical applications of electroporation, IEEE Transactions on Plasma Science, Feb. 2000, vol. 28, No. 1, pp. 206-222

Ivanusa, et al, MRI macromolecular contrast agents as indicators of changed tumor blood flow, Radiol Oncol, 2001, 35, 2, pp. 139-147.

Ermolina, et al, Study of normal and malignant white blood cells by time domain dielectric spectroscopy, IEEE Transactions on Dielectrics and Electrical Insulation, Apr. 2001, vol. 8, No. 2, pp. 253-261.

Carson, et al, Improving patient satisfaction, BPH management strategies, Supplement to Urology Times, May 2001, Vo. 29, Suppl. 1, pp. 1-22.

Beebe, et al, Nanosecond pulsed electric field (nsPEF) effects on cells and tissues: Apoptosis induction and tumor growth inhibition, IEEE, 2002, pp. 211-215.

N/A, When patient satisfaction is your goal, Precision Office TUNA System, VidaMed, Inc.

Chandrasekar, et al, Transurethral needle ablation of the prostate (TUNA)—A prospective study, six year follow up, pp. 1210.

N/A, Highlights from worldwide clinical studies, Transurethral needle ablation (TUNA), Vidamed's Office TUNA System, VidaMed, Inc. , pp. 1-4.

Schoenbach, et al, Intracellular effect of ultrashort electrical pulses, Bioelectromagnetics, 2001, 22, pp. 440-448.

Cemazar, et al, Electroporation of human microvascular endothelial cells: evidence for an anti-vascular mechanism of electrochemotherapy, British Journal of Cancer, 2001, 84, 4, pp. 565-570.

Kotnik, et al, Cell membrane electropermeabilization by symmetrical biopolar rectangular pulses, Part I. Increased efficiency of permeabilization, Bioelectrochemistry, 2001, 54, pp. 83-90.

Kotnik, et al, Cell membrane electropermeabilization by symmetrical biopolar rectangular pulses, Part II. Reduced electrolytic contamination, Bioelectrochemistry, 2001, 54, pp. 91-95.

Lebar, Miklavcic, Cell electropermeabilization to small molecules in vitro: control by pulse parameters, Radiol Oncol, 2001, 35, 3, pp. 193-202.

Naslund, Cost-effectiveness of minimally invasive treatments and transurethral resection (TURP) in benign prostatic hyperplasia (BPH), Unveristy of Maryland School of Medicine, 2001, pp. 1213.

Davalos, et al, A feasibility study for electrical impedance tomography as a means to montior tissue electroporatioin or molecular medicien, IEEE Transactions on Biomedical Engineering, Apr. 2002, vol. 49, No. 4, pp. 400-403.

Jossinet, et al, Electrical impedance end-tomography: Imaging tissue from inside, IEEE Transactions on Medical Imaging, Jun. 2002, vol. 21, No. 6, pp. 560-565.

Lebar, et al, Inter-pulse interval between rectangular voltage pulses affects electroporation threshold of artifical lipid bilayers, IEEE Transactions on Nanobioscience, Sep. 2002, vol. 1, No. 3, pp. 116-120.

Sersa, et al, Reduced blood flow and oxygenation in SA-I tumors after electrochemotherapy with cisplatin, 2003, 87, pp. 1047-1054.

Davalos, Real-time imaging for molecular medicine through electrical impedance tomography of electroporation, Dissertation, Univeristy of California, Berkeley.

Rubinsky, Irreversible electroporation in medicine, Technology in Cancer Research and Treatment, Aug. 2007, vol. 6, No. 4, pp. 255-259.

Onik, et al, Irreversible electroporation: Implications for prostate ablation, Technology in Cancer Research and Treatment, Aug. 2007, vol. 6, No. 4, pp. 295-300.

Lee, et al, Imaging guided percutaneous irreversible electroporation: Ultrasound and immunohistological correlation, Technology in Cancer Research and Treatment, Aug. 2007, vol. 6, No. 4, pp. 287-293.

Bertacchini, et al, Design of an irreversible electroporation system for clinical use, Technology in Cancer Research and Treatment, Aug. 2007, vol. 6, No. 4, pp. 313-320.

Al-Sakere, et al, A study of the immunological response to tumor ablation with irreversible electroporation, Technology in Cancer Research and Treatment, Aug. 2007, vol. 6, No. 4, pp. 301-305.

Fischbach, et al, Engineering tumors with 3D scaffolds, Nature Methods, Sep. 2, 2007, vol. 4, No. 10, pp. 855-860.

Ivorra, Rubinsky, In vivo electrical impedance measurements during and after electroporation of rat liver, Bioelectrochemistry, Oct. 21, 2007, 70, pp. 287-295.

Yao, et al, Study of transmembrane potentials of inner and outer membranes induced by pulsed-electric-field model and simulation, IEEE Transactions on Plasma Science, Oct. 2007, vol. 35, No. 5, pp. 1541-1549.

(56) References Cited

OTHER PUBLICATIONS

Corovic, et al, Analytical and numerical quantification and comparison of the local electric field in the tissue for different electrode configurations, BioMedical Engineering Online, Oct. 15, 2007, 6, 37, pp. 1-14.

Schoenbach, et al, Bioelectric effects of intense nanosecond pulses, IEEE Transactions on Dielectric and Electrical Insulation, 2007, vol. 14, Iss. 5, pp. 1088-1109.

Al-Sakere, et al, Tumor ablation with irreversible electroporation, PLoS One, Nov. 7, 2007, Iss. 11, e1135, pp. 1-8.

Hall, et al, Nanosecond pulsed electric fields have differential effects on cells in the S-phase, DNA and Cell Biology, 2007, vol. 26, No. 3, pp. 160-171.

He, et al, Nonlinear current response of micro electroporation and resealing dynamics for human cancer cells, Bioelectrochemistry, Jan. 29, 2008, 72, pp. 161-168.

Ott, et al, Perfusion-decellarized matrix: using nature's platform to engineer a bioartificial heart, Nature Medicine, Jan. 13, 2008, vol. 14, No. 2, pp. 213-221.

Ron, et al, Cell-based screening for membranal and cytoplasmatic markers using dielectric spectroscopy, Biophysical Chemistry, Mar. 29, 2008, 135, pp. 59-68.

Garcia, et al, Irreversible electroporation (IRE) to treat brain tumors, Proceedings of the ASME 2008 Summer Bioengineering Conference (SBC2008), Jun. 25, 2008, pp. 6-7.

Davalos, Rubinsky, Temperature considerations during irreversible electroporation, International Journal of Heat and Mass Transfer, Jun. 14, 2008, 51, pp. 5617-5622.

Dahl, et al, Nuclear shape, mechanics and mechanotransduction, Circulation Research, Jun. 6, 2008, 102, pp. 1307-1318.

Seidler, et al, A Cre-loxP-based mouse model for conditional somatic gene expression and knockdown in vivo by using avian retroviral vectors, PNAS, Jul. 22, 2008, vol. 105, No. 29, pp. 10137-10142.

Maor, et al, Intravascular irreversible electroporation: Theoretical and experimental feasibility study, 30th Annual International IEEE EMBS Conference, IEEE, Aug. 20, 2008, pp. 2051-2054.

Maor, et al, Irreversible electroporation attenuates neointimal formation after angioplasty, IEEE Transactions on Biomedical Engineering, Sep. 2008, vol. 55, No. 9, pp. 2268-2274.

Jensen, et al, Tumor volume in subcutaneous mouse xenografts measured by microCT is more accurate and reproducible than determined by 18F-FDG-microPET or external caliper, BMC Medical Imaging, Oct. 16, 2008, 8, 16,m pp. 1-9.

Rubinsky, et al, Optimal parameters for the destruction of prostate cancer using irreversible electroporation, The Journal of Urology, Dec. 2008, vol. 180, pp. 2668-2674.

Daud, et al, Phase I trial of Interleukin-12 plasmid electroporation in patients with metastatic melanoma, Journal of Clinical Oncology, Dec. 20, 2008, vol. 26, No. 36, pp. 5896-5903.

Flanagan, et al, Unique dielectric properties distinguish stem cells and their differentiated progeny, Stem Cells, 2008, 26, pp. 656-665.

Mali, et al, The effect of electroporation pulses on functioning of the heart, Med Biol Eng Comput, 2008.

Kuthi, Gundersen, Nanosecond uplse generator with scalable pulse amplitude, IEEE, 2008, pp. 65-68.

Craiu, Scadden, Chapter 22 flow electroporation with pulsed electric fields for purging tumor cells, Electroporation Protocols: Preclinical and Clinical Gene Medicine, Methods in Molecular Biology, vol. 423, pp. 301-310.

Mir, Chapter 1 application of electroporation gene therapy: Past, current and future, Electroporation Protocols: Preclinical and Clinical Gene Medicine, Methods in Molecular Biology, vol. 423, pp. 3-17.

Lin, Lee, An optically induced cell lysis device using dielectrophoresis, Applied Physics Letters, Jan. 20, 2009, 94, 033901, pp. 1-3.

Kroeger, et al, Curvature-driven pore growth in charged membranes during charge-pulse and voltage-clamp experiments, Biophysical Journal, Feb. 2009, 96, 3, pp. 907-916.

Maor, et al, Non thermal irreversible electroporation: Novel technology for vascular smooth muscle cells abation, PLoS One, Mar. 9, 2009, vol. 4757-, Iss. 3, e4757, pp. 1-9.

Shafiee, et al, A preliminary study to delineate irreversible electroporation from thermal damage using the Arrhenius equation, Journal of Biomedical Engineering, Jul. 2009, vol. 131, 074509, pp. 1-5.

Granot, et al, In vivo imaging of irreversible electroporation by means of electrical impedance tomography, Phys. Med. Biol., Jul. 30, 2009, 54, pp. 4927-4943.

Daniels, Rubinsky, Electrical field and temperature model of nonthermal irreversible electroporation in heterogeneous tissues, Journal of Biomedical Engineering, Jul. 2009, vol. 131, 071006, pp. 1-12.

Esser, et al, Towards solid tumor treatment by nanosecond pulsed electric fields, Technology in Cancer Research and Treatment, Aug. 2009, vol. 8, No. 4, pp. 289-306.

Ivorra, et al, In vivo electrical conductivity measurements during and after tumor electroporation: conductivity changes reflect the treatment,Phys. Med. Biol., Sep. 17, 2009, 54, pp. 5949-5963.

Garcia, et al, Pilot study of irreversible electroporation for intracranial surgery, 31st Annual International Conference of the IEEE EMBS, IEEE, Sep. 2, 2009, pp. 6513-6516.

Hong, et al, Cardiac ablation via electroporation, 31st Annual International Conference of the IEEE EMBS, IEEE, Sep. 2, 2009, pp. 3381-3384.

Neal, Davalos, The feasibility of irreversible electroporation for the treatment of breast cancer and other heterogeneous systems, Annals of Biomedical Engineering, Dec. 2009, vol. 37, No. 12, pp. 2615-2625.

Sharma, et al, Review on thermal energy storage with phase change materials and applications, Renewable and Sustainable Energy Reviews, 2009, 13, pp. 318-345.

Ibey, et al, Selective cytotoxicity of intense nanosecond-duration electric pulses in mammalian cells, Biochim Biophys Acta, Nov. 2010, 1800, 11, pp. 1210-1219.

Tsivian, Polascik, Recent advances in focal therapy of prostate and kidney cancer, Medicine Reports, Jan. 18, 2010, 2, 1, pp. 1-3.

Maor, Rubinsky, Endovascular nonthermal irreversible electroporation: A finite element analysis, Journal of Biomedical Engineering, Feb. 7, 2010, vol. 132, 031008, pp. 1-7.

Choi, et al, Preclinical analysis of irreversible electroporation on rat liver tissues using a microfabricated electroporator, Tissue Engineering Part C, 2010, vol. 16, No. 6, pp. 1245-1253.

Verbridge, et al, Oxygen-controlled three-dimensional cultures to analyze tumor angiogenesis, Tissue Engineering, Part A, Apr. 9, 2010, vol. 16, No. 7, pp. 2133-2141.

Lee, et al, Advanced hepatic ablation technique for creating complete cell death: Irreversible electroporation, 2010, Radiology, vol. 255, No. 2, pp. 426-433.

Ball, et al, Irreversible electroporation: A new challenge in "out of the operating theater" anesthesia, Anesth Analg, May 2010, 110, pp. 1305-1309.

Laufer, et al, Electrical impedance characterization of normal and cancerous human hepatic tissue, Physiol Meas, 2010, 31, pp. 995-1009.

Mir, Orlowski, Introduction: Electropermeabilization as a new drug delivery approach, Methods in Molecular Medicine, 2000, vol. 37, pp. 99-117.

O'Brien, et al, Investigation of the Alamar Blue (resarzurin) fluorescent dye for the assessment of mammalian cell cytotoxicity, Eur J Biochem, 2000, 267, pp. 5421-5426.

Wright, On a relationship betweene the arrhenius parameters from thermal damage studies, Technical Brief, Journal of Biomechanical Engineering, Transactions of the ASME, Apr. 2003, vol. 125, pp. 300-304.

Heczynska, et al, Hypoxia promotes a dedifferentiated phenotype in ductal breast carcinoma in situ, Cancer Research, Apr. 1, 2003, 63, pp. 1441-1444.

Ivorra, Bioimpedance monitoring for physicians: an overview, Biomedical Applications Group, Centre Nacional de Microelectronica, Jul. 2003, pp. 1-35.

Weaver, Electroporation of biological membranes from multicellular to nano scales, IEEE Transactions on Dielectrics and Electrical Insulation, Oct. 2003, vol. 10, No. 5, pp. 754-768.

(56) References Cited

OTHER PUBLICATIONS

Dev, et al, Electric field of a six-needle array electrode used in drug and DNA delivery in vivo: Analytical versus numerical solution, IEEE Transactions on Biomedical Engineering, Nov. 2003, vol. 50, No. 11, pp. 1296-1300.
Rajagopal, Rockson, Coronary restenosis: A review of mechanisms and management, The American Journal of Medicine, Nov. 2003, vol. 115, pp. 547-553.
Sersa, et al, Tumor blood flow modifying effects of electrochemotherapy: a potential vascular targeted mechanism, Radiol Oncol, 2003, 37, 1, pp. 43-48.
Davalos, et al, Theoretical analysis of the thermal effects during in vivo tissue electroporation, Bioelectrochemistry, 2003, 61, pp. 99-107.
Gothelf, et al, Electrochemotherapy: results of cancer treatment using enhanced delivery of bleomycin by electroporation, Cancer Treatment Reviews, 2003, 39, pp. 371-387.
Bancroft, et al, Design of a flow perfusion bioreactor system for bone tissue-engineering applications, Tissue Engineering, 2003, vol. 9, No. 3, pp. 549-554.
Malpica, et al, Grading ovarian serous carcinoma using a two-tier system, Am J Surg Pathol, Apr. 2004, vol. 28, No. 4, pp. 496-504.
Davalos, et al, Electrical impedance tomography for imaging tissue electroporation, IEEE Transactions on Biomedical Engineering, May 2004, vol. 51, No. 5, pp. 761-767.
Albright, et al, Performance and complicatioins associated with the Synchromed 10-ml infusion pump for intrathecal baclofen administration in children, J Neurosurg (Pediatrics 2), Aug. 2004, vol. 101, pp. 64-68.
Diederich, et al, Catheter-based ultrasound applicators for selective thermal ablation: progress towards MRI-guided applications in prostate, Int. J. Hyperthermia, Nov. 2004, vol. 20, No. 7, pp. 739-756.
Radeva, et al, Induction of apoptosis and necrosis in cancer cells by electric fields, electromagnetic fields, and photodynamically active quinoids, Electromagnetic Biology and Medicine, 2003, 23, pp. 185-200.
Davalos, et al, Tissue ablation with irreversible electroporation, Annals of Biomedical Engineering, Feb. 2005, vol. 33, No. 2, pp. 223-231.
Sel, et al, Sequential finite element model of tissue electropermeabilization, IEEE Transactions on Biomedical Engineering, May 2005, vol. 52, No. 5, pp. 816-827.
Dean, Nonviral gene transfer to skeletal, smooth, and cardiac muscle in living animals, Am J Physiol cell Physiol, Aug. 2005, 289, pp. C233-C245.
Pavselj, et al, The course of tissue permeabilization studied on a mathematical model of a subcutaenous tumor in small animals, IEEE Transactions on Biomedical Engineering, Aug. 2005, vol. 52, No. 8, pp. 1373-1381.
Paszek, et al, Tensional homeostasis and the malignant phenotype, Cancer Cell, Sep. 2005, vol. 8, pp. 241-254.
Saur, et al, CXCR4 expression increases liver and lung metastasis in a mouse model of pancreatic cancer, Basic-Liver, pancreas, and biliary tract, Gastroenterology, Oct. 2004, 129, pp. 1237-1250.
Knight, et al, Direct imaging of transvenous radiofrequency cardiac ablation using a steerable fiberoptic infrared endoscope, Heart Rhythm Society, Oct. 2005, vol. 2, No. 10, pp. 1116-1121.
Miller, et al, Cancer cells ablation with irreversible electroporation, Technology in Cancer Research and Treatment, Dec. 2005, vol. 4, No. 6, pp. 699-705.
Mir, et al, Electric pulse-mediated gene delviery to various animal tissues, Advances in Genetics, 2005, vol. 54, pp. 84-114.
Nikolski, Efimov, Electroporation of the heart, Europace, 2005, 7, pp. S146-S154.
Machado-Aranda, et al, Gene transfer of the NA+, K+K -ATPase B1 subunit using electroporation increases lung liquid clearance, American Journal of Respiratory and Critical Care Medicine, 2004, vol. 171, pp. 204-211.

Kotnik, Miklavcic, Theoretical evaluation of voltage inducement on internal membranes of biological cells exposed to electric fields, Biophysical Journal, Jan. 2006, vol. 90, pp. 480-491.
Labeed, et al, Differences in the biophysical properties of membrane and cytoplasm of apoptotic cells revealed using dielectrophoresis, Biochimica et Biophysica Acta, Feb. 23, 2006, 1760, pp. 922-929.
Pucihar, et al, Numerical determination of transmembrane voltage indcued on irregularly shaped cells, Annals of Biomedical Engineering, Mar. 18, 2006, vol. 34, No. 4, pp. 642-652.
Gilbert, et al, Decellularization of tissues and organs, Biomaterials, Mar. 7, 2006, 27, pp. 3675-3683.
Edd, et al, In vivo results of a new focal tissue ablation technique: Irreversible electroporation, IEEE Transactions on Biomedical Engineering, Jun. 2006, vol. 53, No. 5, pp. 1409-1415.
Ivorra, Rubinsky, Impedance analyzer for in vivo electroporation studies, Proceedings of the 28th IEEE EMBS Annual International Conference, IEEE, Aug. 30, 2006, pp. 5056-5059.
Carpenter, et al, CellProtiler: image analysis software for identifying and quantifying cell phenotypes, Genome Biology, Oct. 31, 2006, vol. 7, Iss. 10, R100, pp. 1-11.
Kanduser, et al, Cell membrane fluidity related to electroporation and resealing, Eur Biophys J, Oct. 8, 2006, 35, pp. 196-204.
Bolland, et al, Development and characterisation of a full-thickness acellular porcine bladder matrix for tissue engineering, Biomaterials, Nov. 7, 2006, 28, pp. 1061-1070.
Cukjati, et al, Real time electroporation control for accurate and safe in vivo non-viral gene therapy, Bioelectrochemistry, Nov. 10, 2006, 70, pp. 501-507.
Tijink, et al, How we do it: Chemo-electroporation in the head and neck for otherwise untreatable patients, Correspondence, Clinical Otolaryngology, 2006, 31, pp. 447-451.
Marty, et al, Electrochemotherapy—An easy, highly effective and safe treatment of cutaneous and subcutaneous metastases: Results of ESOPE (European Standard Operating Procedures of Electrochemotherapy) study, EJC Supplements, 2006, 4, pp. 3-13.
Soden, et al, Successful application of targeted electrochemotherapy using novel flexible electrodes and low dose bleomycin to solid tumors, Cancer Letters, 2006, 232 pp. 300-310.
Demirbas, Thermal energy storage and phase change materials: An overview, Energy Sources, Part B, 2006, 1, pp. 85-95.
Rubinsky, et al, Irreversible electroporation: A new ablation modality—Clinical implications, Technology in Cancer Research and Treatment, Feb. 2007, vol. 6, No. 1, pp. 1-12.
Zhou, et al, Electroporation-mediated transfer of plasmids to the lung results in reduced TLR9 signaling and Inflammation, Gene Therapy, Mar. 8, 2007, 14, pp. 775-780.
Lavee, et al, A novel nonthermal energy source for surgical epicardial atrial ablation: Irreversible electroporation, The Heart Forum, Mar. 2007, 10, 2, pp. 96-101.
Hall, et al, Nanosecond pulsed electric fields induce apoptosis in p53-wildtype and p53-null HCT116 colon carcinoma cells, Apoptosis, May 23, 2007, 12, pp. 1721-1731.
Sel, et al, Feasibility of employing model-based optimization of pulse amplitude and electrode distance for effective tumor electropereabilization, IEEE Transactions on Biomedical Engineering, May 2007, vol. 54, No. 5, pp. 773-781.
Kirson, et al, Alternating electric fields arrest cell proliferation in animal tumor models and human brain tumor, PNAS Jun. 12, 2007, vol. 104, No. 24, pp. 10152-10157.
Talele, Gaynor, Non-linear time domain model of electropermeabilizationi: Response of a single cell to an arbitary applied electric field, Journal of Electrostatics, Jul. 16, 2007, 65, pp. 775-784.
Esser, et al, Towards solid tumor treatment by irreversible electroporation: Intrinsic redistribution of fields and currents in tissue, Technology in Cancer Research and Treatment, Aug. 2007, vol. 6, No. 4, pp. 261-273.
Maor, et al, The effect of irreversible electroporation on blood vessels, Technology in Cancer Research and Treatment, Aug. 2007, vol. 6, No. 4, pp. 307-312.

(56) References Cited

OTHER PUBLICATIONS

Edd, Davalos, Mathematical modeling of irreversible electroporation for treatment planning, Technology in Cancer Research and Treatment, Aug. 2007, vol. 6, No. 4, pp. 275-286.

* cited by examiner

METHOD FOR TREATING A TUBULAR ANATOMICAL STRUCTURE

CROSS REFERENCE TO RELATED APPLICATIONS

The present application is a continuation of U.S. patent application Ser. No. 14/134,109, filed Dec. 19, 2013, which is a continuation of U.S. patent application Ser. No. 12/820,955, filed Jun. 22, 2010, now U.S. Pat. No. 8,634,929, which is a continuation of U.S. patent application Ser. No. 11/347,965, now U.S. Pat. No. 7,765,010, filed Feb. 6, 2006, which is a division of U.S. patent application Ser. No. 10/217,749, now U.S. Pat. No. 6,994,706, filed Aug. 13, 2002, which claims priority to U.S. Provisional Application No. 60/311,792, filed Aug. 13, 2001 and to U.S. Provisional Application No. 60/325,994, filed Oct. 1, 2001, all of which are incorporated herein by reference.

FIELD OF INVENTION

The present invention relates generally to the therapeutic treatment of tissue and more particularly, to a method for treating muscle tension on a tubular anatomical structure of a patient.

DESCRIPTION OF THE RELATED ART a. Electroporation:

Biophysical phenomenon "electroporation" (EP) refers to the use of electric field pulses to induce microscopic aquatic pores—"electropores"—in the lipid cell membranes. Depending on the parameters of the electric pulses, electroporated cell can survive the pulsing or die. The cause of death of an electroporated cell is believed to be a chemical imbalance in the cell, resulted from the fluid communication with the extra cellular environment through the pores. The number and size of electropores depend on both, the amplitude of electric field pulse E and the pulse duration t. Electroporation is observed for pulse durations in the range from tens of microseconds to hundreds of milliseconds. For a given duration of a pulse and below a certain limit of the electric field amplitude, no pores are induced at all. This limit is different for different cells, particularly, for cells of different sizes. The smaller the size of a cell, the higher the electric field required to induce pores and thus the higher the limit is. Above the lower limit the number of pores and their effective diameter increases proportionally with both the amplitude E and duration t.

Until the upper limit of electroporation is achieved, the cells survive pulsing and restore their viability thereafter. Above the upper limit, the pore diameters and number become too large for a cell to survive. The irreversibly chemically imbalanced cell cannot repair itself by any spontaneous or biological process and dies. To kill a cell, a potential in the range of 2 to 4 V should be applied along the cell. The cell killing by electroporation is a probabilistic process, increasing the number of applied pulses leads to increased probability of cell killing, approximately equal to the increase in the total duration of the electric pulse.

The survivability of electroporated cells depends significantly on their temperature. At higher temperature cells are more vulnerable, the amplitude and duration of the electric pulses required for cell killing are lower. This experimental fact is explained by two underlying phenomena: at higher temperatures cells are less stable biochemically because of more intense metabolism, and, secondly, at elevated temperatures the strength of lipid membranes decreases, which facilitates creating larger pores or irreversible rupture. At lower temperatures (10 to 20 degrees C.) cells are more resistant to electroporation and can survive two to three times higher voltages than that at the body temperature.

b. The Prostate Gland and Benign Prostatic Hyperplasia:

The prostate is a walnut-sized gland that forms part of the male reproductive system. The gland consists of several lobes, or regions, enclosed by a dense fibrous capsule. It is located between the bladder and the rectum and wraps around the urethra, the tube that carries urine out from the bladder through the penis. There are generally three glandular zones in a prostate gland: central, peripheral and transitional. The transitional zone is located right behind the place where the seminal vesicles are merging with urethra. This transitional zone tends to be predisposed to benign enlargement. The prostate gland is generally composed of smooth muscles and glandular epithelial tissue. The glandular epithelial tissue produces prostatic fluid. The smooth muscles contract during sexual climax and squeeze the prostatic fluid into the urethra as the sperm passes through the ejaculatory ducts and urethra. Prostatic fluid secreted by the prostate gland provides nutrition for ejaculated spermatozoids increasing their mobility and improves the spermatozoids chances for survival after ejaculation by making the environment in the vaginal canal less acidic.

The prostate reaches its normal size and weight (about 20 grams) soon after puberty. The size and weight of the prostate typically remain stable until the individual reaches his mid-forties. At this age, the prostate typically begins to enlarge through a process of excessive cell proliferation, called benign prostatic hyperplasia (BPH). This overgrowth can occur in both smooth muscle and glandular epithelial tissues and has been attributed to a number of different causes, including hormones and growth factors as well as generally to the aging process.

Benign prostate hyperplasia can cause distressing urination symptoms. As the disease progresses the dense capsule surrounding the enlarging prostate prevents it from further expansion outward and forces the prostate to press against the urethra, partially obstructing the urine flow. The tension in the smooth muscles of the prostate also increases which causes further compression of the urethra and reduction of the urine flow. Some symptoms of BPH stem from the gradual loss of bladder function leading to an incomplete emptying of the bladder. The symptoms can include straining to urinate, a weak or intermittent stream, an increased frequency of urination, pain during urination, and incontinence—the involuntary loss of urine following an uncontrollable sense of urgency. These symptoms alone can negatively affect the quality of life of effected men. Left untreated, BPH can cause even more severe complications, such as urinary tract infection, acute urinary retention, and uremia.

Before age 40, only 10% of men have benign prostatic hyperplasia; but by age 80, about 80% have signs of this condition. Benign prostatic hyperplasia is the most common non-cancerous form of cell growth in men. About 14 million men in US have BPH, and about 375,000 new patients are diagnosed every year.

For many years, researchers have tried to find medications to shrink the prostate or at least stop its growth. Between 1992 and 1997, the FDA approved four drugs: finasteride, terazosin, tamsulosin, and doxazosin for treatment of BPH.

Finasteride (Proscar) inhibits production of hormone DHT. DHT is one of the hormones that have been found to be involved in prostate enlargement. Treatment with Finasteride has been shown to actually shrink the prostate in some men.

Terazosin (Hytrin), doxazosin (Cardura), and tamsulosin belong to the class of drugs known as alpha-blockers. Alpha-blockers act by relaxing the smooth muscle of the prostate and bladder to improve urine flow and reduce bladder outlet obstruction. In men with severe symptoms, though, these medications are not curative. They can delay but not prevent the eventual need for surgery.

Regardless of the efficacy of any drug treatment, the long term exposure to xenobiotic compounds may produce additional unwanted side effects that are not realized until years after treatment. Accordingly, a need exists for an apparatus and method for the treatment of BPH that does not require the introduction of xenobiotic compounds.

For men with the most severe symptoms, surgery is generally considered to be the best long-term solution. There are several surgical procedures that have been developed for relieving symptoms of BPH. However, all of them are very morbid, require a long hospital stay, generally require the use of general anesthesia, suffer from significant side effects, and have possible complications.

In recent years, a number of procedures have been introduced that are less invasive than surgery. One such procedure is the transurethral microwave thermal therapy described in U.S. Pat. No. 5,575,811. In transurethral microwave thermal therapy, a Foley-type catheter containing a microwave antenna is placed within the urethra. The microwave antenna positioned adjacent to the transitional zone of the prostate, where BPH is located, allows selective heating of the prostate. Maintaining the temperature above 45.degree. C. during about one hour session leads to necrosis of the tissues and subsequent reabsorption of necrotic tissue by the body.

Another recently developed non-invasive technique is transurethral needle ablation (TUNA). TUNA is described in U.S. Pat. No. 6,241,702. TUNA uses low level radio frequency (RF) energy to heat the prostate. Using TUNA, two separate needles are inserted into prostate through the urethra. Several watts of RF energy is applied to each needle to cause thermal necrosis of the prostate cells around the needles. Application of this treatment to several sites of the prostate typically results in sufficient necrosis to relieve symptoms of the BPH.

While generally successful, the microwave and RF therapies are relatively long procedures. Also, because of the poor temperature control of the heated volume, the volume of removed tissue is often not sufficient for the long term relief of the symptoms and/or the healthy tissue of the urethra is damaged. A damaged urethra is capable of restoring itself, but the healing is a long morbid process accompanied by sloughing of the necrotic tissue into urethra and excreting it during urination.

Therefore, a need exists for a minimally invasive therapy for treatment of BPH that requires shorter treatment times and is less morbid than existing therapies.

SUMMARY OF THE INVENTION

The present invention satisfies the above-listed needs and provides additional improvements and advantages that will be recognized by those skilled in the art upon review of the following description and figures.

The object of the present invention is to provide a treatment that causes necrosis of BPH in a shorter period of time than that of the existing transurethral thermal therapies.

Another object of the present invention is to destroy nerves causing tension in the fibre-muscular tissue and thus achieve relaxation of the muscles contracting the urethra.

Another object of the present invention is to decrease morbidity of the treatment.

Another object of the present invention is to improve control of the volume in the prostate where necrosis occurs, avoid sloughing of the necrotic tissue through the urethra and decrease the damage to the urethra itself.

A shorter treatment time is achieved by applying to the tumorous tissue multiple high voltage pulses that cause necrosis of BPH by electroporation.

In one aspect, the present invention provides a method for treating cells in a living human body. In certain embodiments, the method includes the steps of advancing into a tubular anatomical structure a catheter having a first and second electrode, and applying, using at least one of the advanced electrodes, an electrical energy in an amount sufficient to destroy elongate cells.

In another aspect, the present invention provides a method for treating cells in a living human body including advancing into a tubular anatomical structure a catheter having a first and second electrode, applying, using at least one of the advanced electrodes, an electrical energy in an amount sufficient to destroy elongate cells, where the step of applying includes applying the electrical energy in a direction which is substantially radial to the tubular anatomical structure.

In yet another aspect, the present invention provides a method for treating elongate cells in a living human body, the method including advancing into a tubular anatomical structure a catheter having a first and second electrode, positioning the electrodes of the advanced catheter near a target area containing elongate cells, applying, using at least one of the positioned electrodes, an electrical energy in an amount sufficient to destroy the elongate cells in the target area, wherein the step of applying includes applying the electrical energy in a direction substantially along the length of the elongate cells.

In yet another aspect, the present invention provides a method for treating elongate cells in a living human body, the method including advancing into the tubular anatomical structure a catheter having a first and second electrode, positioning the electrodes of the advanced catheter near a target area containing elongate cells, applying, using at least one of the positioned first and second electrodes, an electrical energy in an amount sufficient to destroy the elongate cells in the target area, wherein the step of applying includes applying the electrical energy in a direction which is substantially radial to the tubular anatomical structure.

The present invention, as well as its various features and advantages, will become evident to those skilled in the art when the following description of the invention is read in conjunction with the accompanying drawings as briefly described below and the appended claims. Throughout the drawings, like numerals refer to similar or identical parts.

Figure 1:
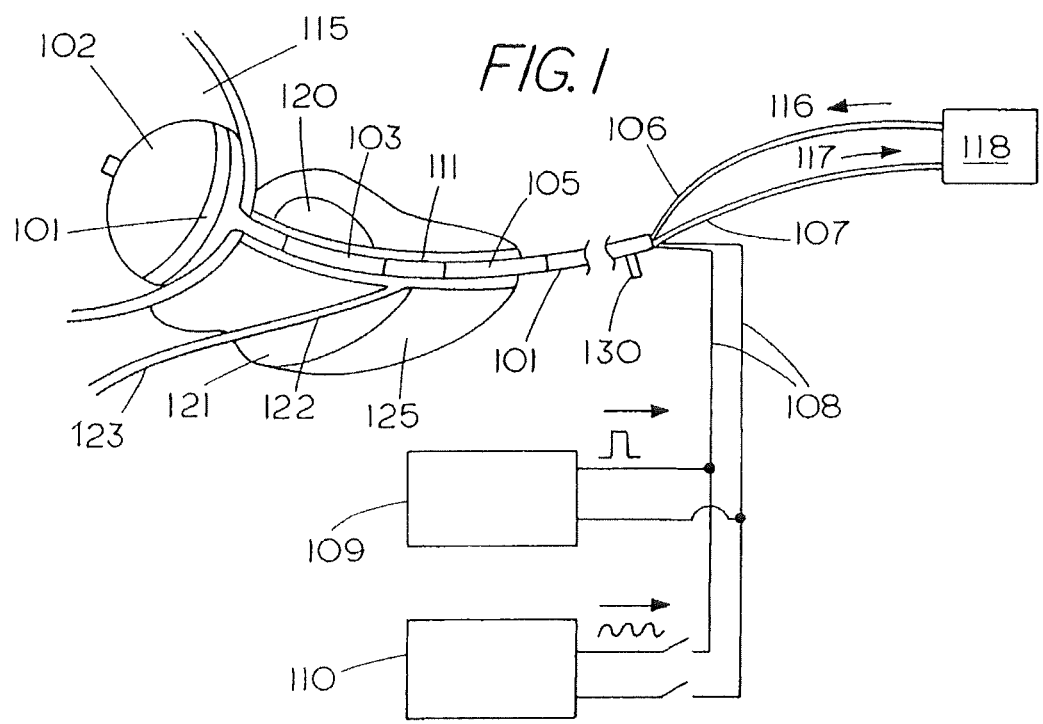
FIG. 1 is a schematic illustration of an embodiment of an apparatus for treatment of BPH in accordance with the present invention.

All figures are drawn for ease of explanation of the basic teachings of the present invention only; the extensions of the figures with respect to number, position, relationship and dimensions of the parts to form the preferred embodiment will be explained or will be evident to those skilled in the art after the following description has been read and understood. Further, the exact dimensions and dimensional proportions to conform to specific force, weight, strength, and similar requirements will likewise be evident to those skilled in the art after the following description has been read and understood.

Where used in various figures or on multiple occasions within the same figures, the same numerals generally designate the same or similar parts or features. Furthermore, when the terms "vertical," "horizontal," "top," "bottom," "right," "left," "forward," "rear," "first," "second," "inside," "outside," and similar terms are used, the terms should be understood to reference only the structure shown in the drawings as it would generally appear to a person viewing the drawings and utilized only to facilitate describing the illustrated embodiment.

DETAILED DESCRIPTION OF THE INVENTION

In one aspect, the current invention in part stems from recognition of the fact that the effect of electroporation on tissue can be modulated by selecting a specific direction relatively to a cell for application of a pulsed electric field. For elongated cells similar to muscle fibers the length-to-width ratio can be as high as 20 to 30. For the nerve cells this ratio can be even higher. The vulnerability of cells to electroporation is different for different directions of the applied field. It depends on the size of a cell in the direction of the applied field. In other words, elongated cells can be killed with significantly lower electric field if the field is applied along the cells, if the field is applied across the cell the cell is capable of surviving much higher amplitudes of the electric field.

In the current invention relief of symptoms is achieved by electroporation treatment, which is used to create a necrotic zone in the BPH tissue around the urethra. Necessary control of the volume of the necrotic area, its shape and location relatively to the healthy tissues of the prostate and urethra can be provided by a system of electrodes generating electric field in the area of the benign enlargement of the prostate. Application of multiple electrical pulses with appropriate voltage and duration leads to necrosis of prostatic tissues around the urethra.

Anatomically, predominant direction of fibers in the fibro-muscular glandular tissue of BPH is radial to the urethra. In the present invention the preferred direction of applied electric field is also radial to the urethra, coinciding with the direction of fibers. Application of the electroporating pulses along the muscular fibers and nerves that anatomically follow them selectively kills both types of fibers. Thus two intermediate goals of the present therapy become achieved: first, a significant volume of necrotic BPH tissue around the urethra is created; second, the nerves causing elevation in tension of the muscle fibers are destroyed. Removal of the necrotic tissue by macrophages decreases the total volume of BPH and reduces pressure on the urethra. Destruction of the nerves results in relaxation of the prostate. Subsequently, both effects contribute to the improvement of the urethra and bladder functions after treatment.

To apply a pulsed electric field to the BPH region in the transition zone of the prostate, a set of electrodes is placed into the urethra (and the bladder) on the urethral catheter. In other embodiments of the invention, external electrodes are utilized or needle-type electrodes may be introduced into the volume of BPH tissue. The electrodes are electrically connected to a generator producing high voltage pulses, the amplitude and duration of which are selected to provide electric field in the prostatic tissue exceeding the upper electroporation limit for the fibro-muscular cells. Duration of pulses may be selected from the range of 10 microseconds to 500 milliseconds. The amplitude and number of pulses are preselected to cause necrosis of the BPH cells, mainly muscle cells and nerves.

Sphincters, located on the urethra anterior and posterior to the prostate gland, consist of smooth muscle cells wrapped circumferentially around the urethra. They control shutting down the flow of urine from the bladder and should be preserved during the treatment. Radial electric field applied to the prostate is transversal to the sphincter muscle fibers to which they are relatively resistant. However, to ensure that electroporation injury to the sphincters is avoided, the electrode in the urethra between the sphincters should not be positioned too close to them. For the same reason the amplitude of the electric field during treatment should be selected not to exceed the upper electroporation limit of the sphincter muscles in the transversal direction.

In another aspect, the present invention provides an apparatus and method for treatment of the prostate. The invention is generally described in the context of an apparatus and method for the treatment of BPH as a specific example for illustrative purposes only. Upon review of the following description and figures, those skilled in the art will understand that an apparatus in accordance with the present invention may be used for a wide variety of indications.

An apparatus for treatment of the prostate in accordance with the present invention is shown in FIG. 1. A Foley type urethral catheter 101 includes balloon 102 at its distal end. Urethral catheter 101 is introduced into the urethra 111 (411 in FIG. 4) and balloon 102 positioned within the bladder 115. As illustrated, transition zone 120 of the prostate is being treated for BPH. Anatomically, central zone 121, peripheral zone 125 seminal vesicle 123, and ejaculatory duct 122, are illustrated. Ejaculatory duct 122 delivers the sperm into the prostatic urethra during sexual climax. The catheter can include an electrode 103 adjacent to the prostate in the transition zone 120, and an electrode 104, placed into the bladder distally to the urethra or outside of the urethra on the skin (not shown) of the patient.

An implementation of the present invention having three electrodes is shown in FIG. 1: electrode 104 is in the bladder, electrode 103 is adjacent to the transition zone, electrode 105 can be placed proximally to the electrode 103 in the urethra. Placing more than two electrodes allows achieving better concentration of electric field on affected region of the prostate in the transition zone. A port 106 may be provided in the proximal end of the urethral catheter serving as an inlet for the coolant intended to cool the urethra as the prostate is heated. In one aspect, the prostate may be heated using RF. Therefore, an radio frequency (RF) generator 110 is illustrated for exemplary purposes. In this embodiment, a port 107 can also be provided to serve as an outlet for the coolant carrying the heat from the electrodes 103 and 105 via a flexible tube 117 to the coolant system 118. Wires 108 (408 in FIG. 4) can be provided to connect electrodes 103, 104, 105 with a generator 109, sending electroporation pulses to BPH. For purposes of electroporation, generator 109 is typically configured to provide high voltage. During treatment, the urethra may be cooled by a cooling system 118. Outlet 130 is a channel, fluidly connected to the balloon 102 and serving for its inflation in the bladder 115.

Figure 2:
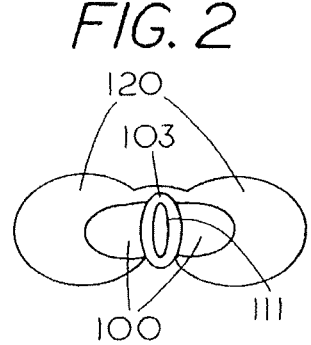
FIG. 2 illustrates a cross-section of the prostate with the urethral catheter in place.

In FIG. 2 a cross-section of an embodiment of the urethral catheter 101 inserted through a prostate is illustrated. Number 100 corresponds to the transition zone of the prostate 120 effected by BPH. Electrode 103 is positioned in the prostate urethra 111.

Figure 3:
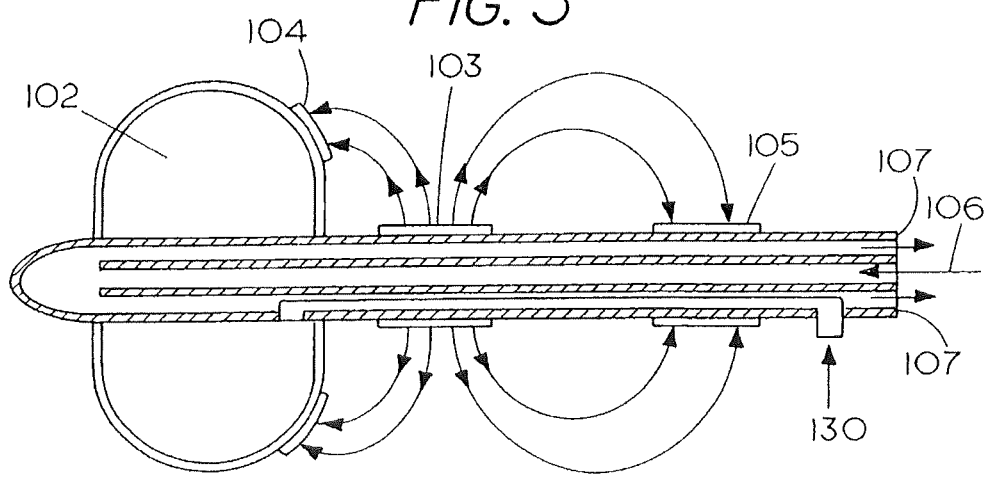
FIG. 3 illustrates a longitudinal section of the urethral catheter.
Figure 4:
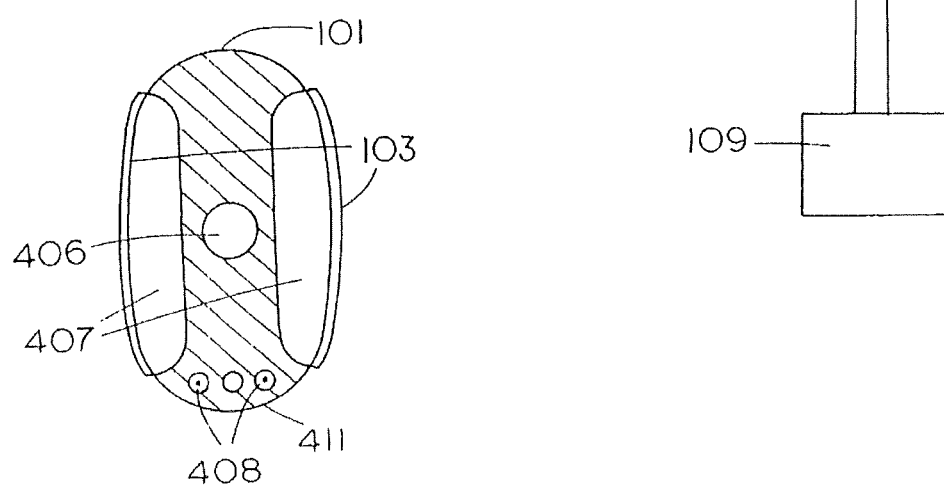
FIG. 4 is an enlarged view of a cross-section of the urethral catheter.

FIG. 3 and FIG. 4 show a longitudinal-section and a cross-section of an embodiment of the urethral catheter 101. Number 103 corresponds to the urethral electrode, 406 is the channel in the catheter, fluidly connected to the inlet 106 at the proximal end of the catheter and accepting the coolant liquid from the pump, not shown in the figure. Number 407 is designated for two channels in the catheter in which the coolant moves back to the proximal end, where through the outlet 107 it is returned to the cooling system.

Figure 5:
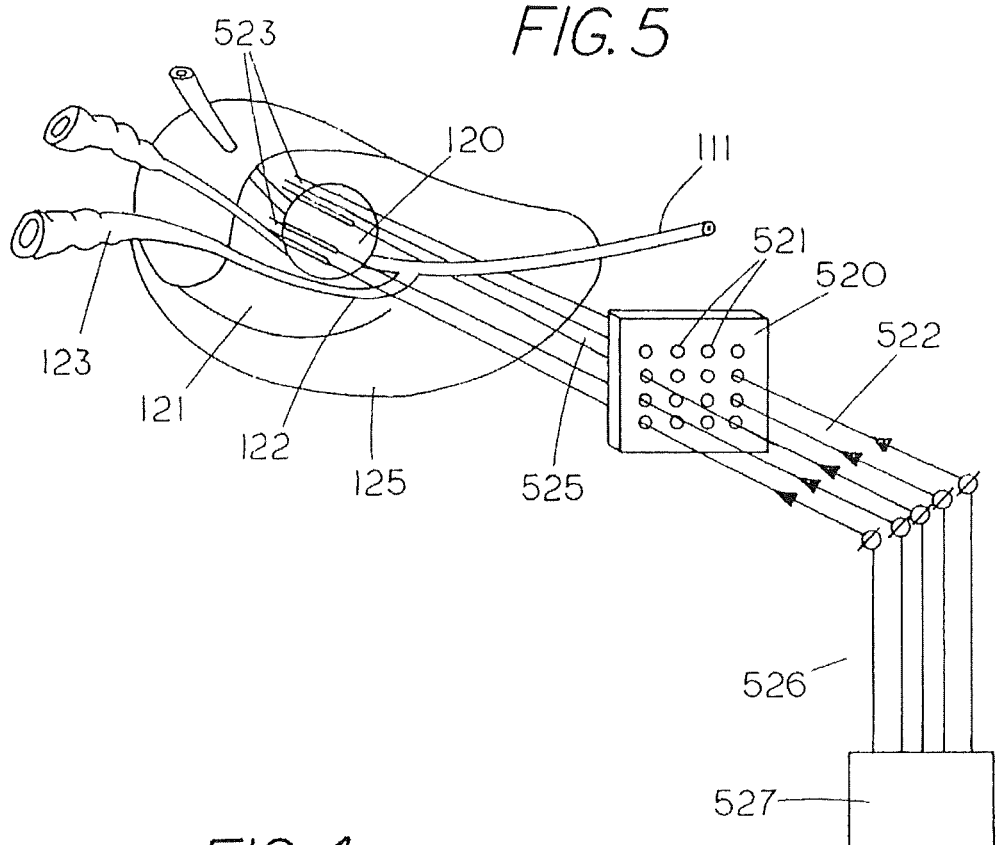
FIG. 5 illustrates an embodiment of an apparatus for treatment of BPH with a perineal needle template.

Another apparatus for implementing the method in accordance with the present invention employing a perineal needle template for placement of electrodes into BPH is depicted in the FIG. 5. Here 520 is a needle perineal template with holes 521 for directing needles having proximal end 522, distal ends 523 and elongated part 525. The proximal ends are electrically connected to multi electrode connector 526, leading to a switch board circuit 527, which, in turn, is connected to the output of the high voltage pulse generator 109.

Figure 6:
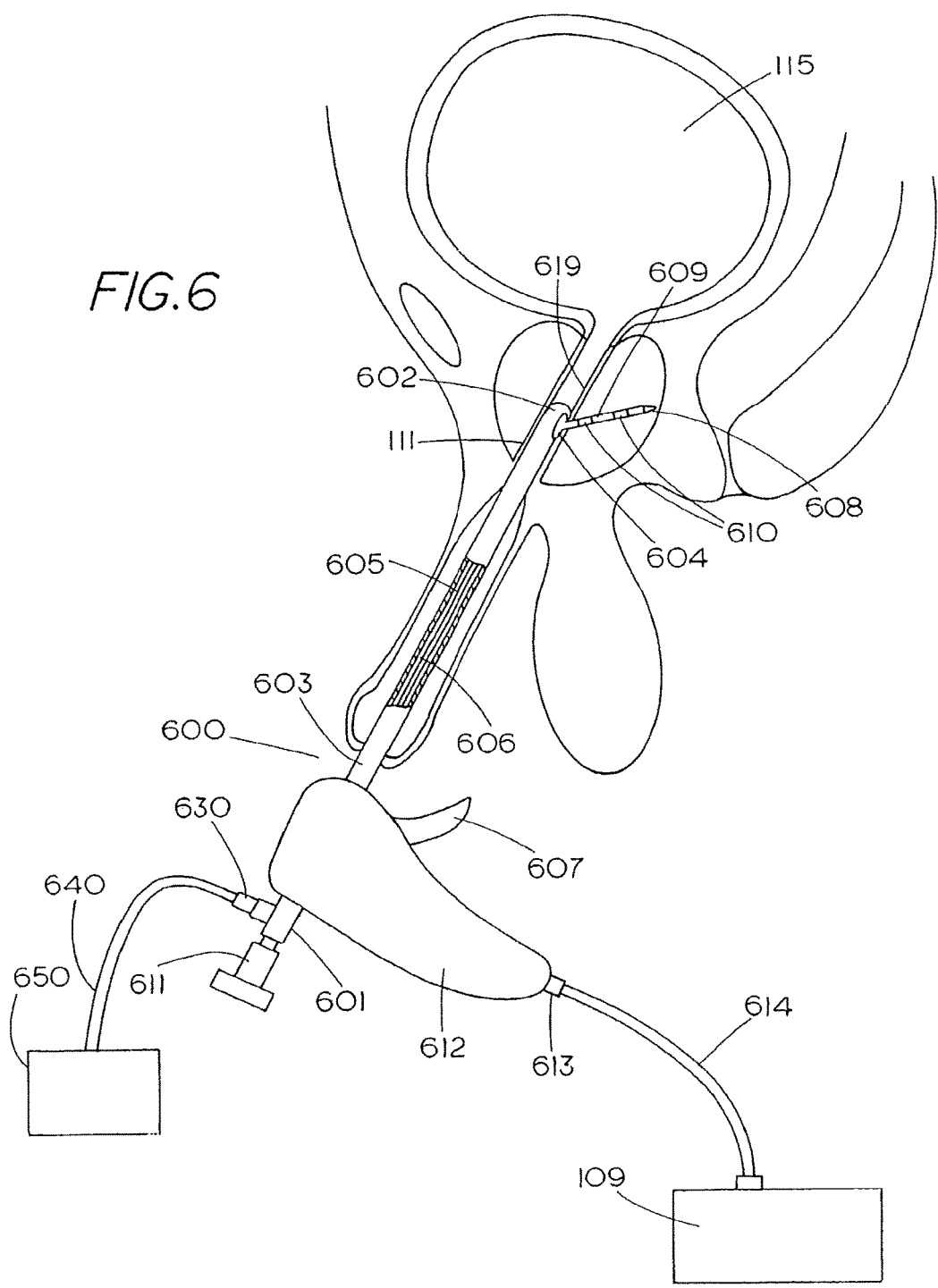
FIG. 6 illustrates an embodiment of an apparatus for treatment of BPH with a urethral probe having a two-electrode needle.

An apparatus for treatment of BPH by electroporation employing a urethral probe—an applicator for placement of electrodes into the prostate via urethra, is shown in FIG. 6. The apparatus comprises a urethral probe 600 having a proximal end 601, elongated member 603 and a distal end 602. The elongated member 603 has a passageway 606 extending from the proximal end of the probe 601 to its distal end 602 and ending at a side port 604 of the probe 601. In the passageway at the proximal end of the probe, an endoscope 611 is introduced. The endoscope has a wide-angle view and allows one to visualize the urethra at the distal end of the probe and thus provides visual control during manipulation of the probe. The endoscope has a fiber optic port 630 secured to a cable 640 connected to a light source 650. The light source 650 provides necessary illumination of the urethra beyond the distal end of the probe. Probe 600 is attached to a control handle piece 612. A flexible needle 605 inside passageway 606 extends throughout its length from the proximal end where it is engaged with a finger 607 via a mechanism adapted for advancement or retraction of the needle along the probe. Being advanced forward, the needle 605 bends at the distal end 602 of the probe 601 and comes out from the side port 604 under an angle close to 90 degrees to the urethra. Control handle piece 612 is used for manipulation of angular and longitudinal positions of the probe in the urethra and placement of the distal end 602 of the probe 601 into several locations along the transition zone of the prostate. The needle has a sharp tip 608 which easily penetrates through the urethra wall 619. Electrodes 610 on the distal part 609 of the needle thus placed into the volume of the BPH. The electrodes are spatially and electrically separated and, being pulsed by a high voltage, are capable of creating a substantial radial electric field along the muscle fibers of the BPH. Two wires leading from the electrodes 610 are extended through the needle 605 to its proximal end and further inside the handle 612 to the connector 613, where they are connected to the cable 614. The cable 614 is connected to the generator 109.

Under endoscopic guidance the probe is introduced by a physician into the patients urethra with the distal end of the probe positioned inside the prostate. The needle of the probe is advanced into the BPH tissue surrounding the urethra and multiple HV pulses are applied. The end point of the electroporation therapy is a significant and stable drop in the electrical resistance of the treated volume. The resistance drop indicates profound electroporation damage to the fibro muscular cells, which later on leads to their necrosis. Overall treatment of one site takes about 10 pulses and several seconds to several tens of seconds in time depending on the repetition rate of the pulse generator.

Figure 7:
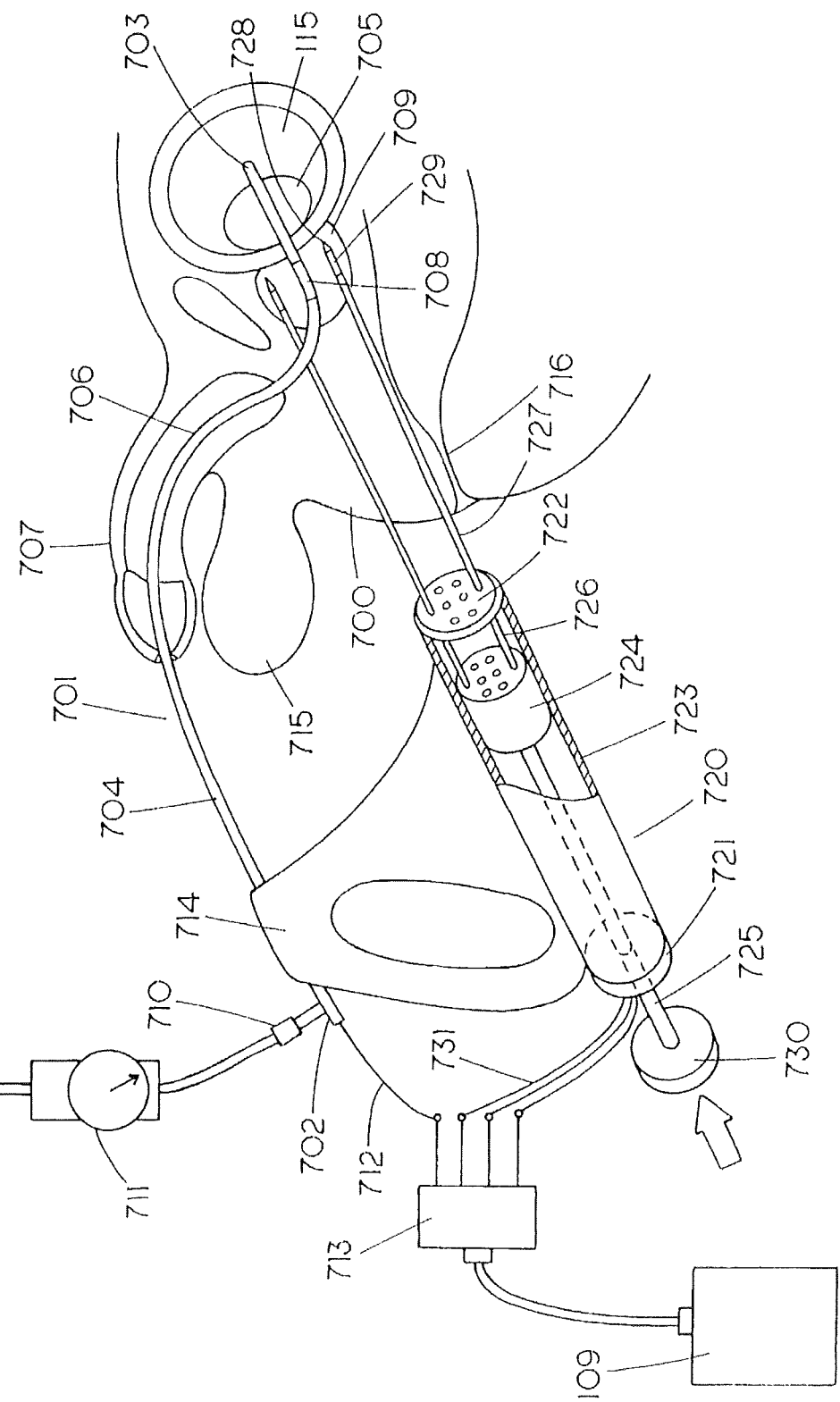
FIG. 7 illustrates a version of the apparatus in accordance with the present invention for treatment of BPH with a urethra-perineal applicator.

Another implementation of the current invention is shown in the FIG. 7. In this version of the apparatus, the needle electrodes are delivered to the prostate by a urethra-perineal apparatus. This apparatus is a combination of a urethral probe carrying a central electrode in the prostatic segment of the urethra and a cartridge of needle electrodes placed into the body of the prostate via a perineal approach. The urethral probe 701 is made of a rigid material, preferably metal, and has a proximal end 702, distal end 703 and an elongated member 704. The distal end of the probe 703 is terminated with a balloon 705 adapted for inflation in the patient bladder 115. During treatment, the probe is introduced into urethra 706 of penis 707 and balloon 705 is inflated. Inflated balloon 705 anchors the probe longitudinally relatively to the bladder and prostate. The length of the urethral electrode and the distance between the electrode and the balloon are selected in such a way that the electrode is placed precisely adjacent to the BPH in the transition zone of the prostate 709. Balloon 705 via a channel inside the probe 701 fluidly communicates with inflation port 710 connected to a syringe 711 actually inflating the balloon. The urethral electrode 708 electrically connected to a wire 712 coming out of the distal end of the probe 702 to switching board circuit 713 whose function is the distribution of the high voltage pulses received from the generator 109 between electrodes placed into prostate during electroporation treatment. The urethral probe 701 is attached to a handle piece 714 used for longitudinal and angular manipulation of the probe. A cartridge 720 used for placement of needle electrodes into prostate via perineal approach is secured at the opposite side of the handle piece 714. The cartridge 720 has a proximal cap 721, a distal cap 722 and a cylinder 723 between them. A piston 724 secured at the end of a plunger 725 slides inside the cylinder 723 between two extreme positions, a proximal and a distal one. In the proximal position the needles are hidden in the cylinder. Being pushed by a knob 730 the piston 724 moves the needles forward through holes 731 in the distal cap 722 forcing the needles to prick perineum 700 situated between scrotum 715 and anus 716 and penetrate prostate 709. An exemplary needle 727 (for simplicity only two needles are shown) has proximal end 726, distal end 728 and electrode 729. The proximal ends of all needles are mounted on the distal surface of the piston 724, electrically insulated from the needles. Through holes on the proximal surface of the piston the needles are electrically connected to wires 731, leading to switchboard circuit 713, used for commutating the high voltage pulsed between separate electrodes or groups of electrodes. The switchboard circuit 713 is coupled to a high voltage pulse generator 109. The needles may be mounted on the piston 724 in two or three rows along concentric circumferences. The electrodes 729, preferentially electrically insulated from the needles, are connected to wires 731, leading to the switchboard circuit 713, with insulated wires disposed inside the hollow needles. The needles in each row may be electrically connected to each other and kept at the same potential during high voltage pulsing. These connections decrease the number of wires that should be placed between the needles and the switchboard circuit 713 and generate an electric field in a predominantly radial direction, the direction that is especially efficient in killing fibro muscular cells positioned radially. The shape of urethral probe 701, its spatial position relatively to the needle cartridge 720 and spacing between the needles are selected to insure that the needles move parallel to the distal part of the urethra and can be placed in the urethra at predetermined radial and longitudinal positions from each other and from the urethra electrode Stated otherwise, the probe member 704 may be configured to include a substantially linear distal end segment that serves to straighten the prostatic urethra when the probe is placed in an operative position in the urethra as shown in the Figure. This distal end segment carries the balloon 705 and the urethral electrode 708. The distal end segment and the needle electrodes 727 each define linear axes that are substantially parallel to each other. With this configuration, then, the needle electrodes 727 may be advanced such that they move substantially parallel to the distal end segment and thus the distal or prostatic urethra. With this configuration of rigid probe, handle, and needle cartridge, the electrodes 729 may be precisely positioned relative to the urethral electrode 708 for application of the electroporation therapy, as will be explained in greater detail with respect to FIG. 8, below.

Figure 8:
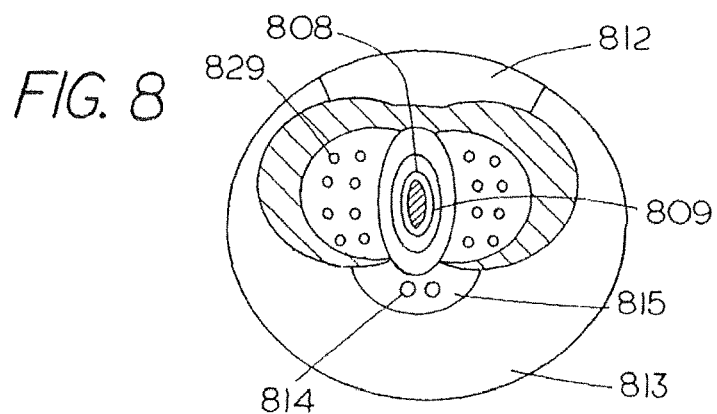
FIG. 8 illustrates a cross-section of the prostate with electrodes of the urethra-perineal applicator in place; and, FIG. 9 illustrates a schematic drawing of needles used in different versions of the apparatus for treatment of BPH in accordance with the present invention.

The relative positioning of the urethral electrode and the needle electrodes in the prostate during treatment is illustrated by FIG. 8. FIG. 8 shows a cross-section of the prostate with all electrodes in place. Numbers 813 and 815 stand for peripheral and central zones of the prostate respectively. Number 812 corresponds to anterior fibro muscular area and 814—for ejaculatory ducts. As can be seen from the FIG. 8, the urethral electrode 808 is placed in the center of the prostate with the needle electrodes 829 positioned around it. A channel 809 connects the distal balloon of the urethral probe and the inflating port located at the proximal end of the probe. Two circumferential rows of needle electrodes are placed concentrically around the urethra. High voltage pulsing applied to the central electrode and any of the rows of electrodes creates a predominantly radially directed electric field. Also, the radial electric field can be created by pulsing the rows of the needle electrodes only, without applying voltage to the central urethral electrode, or it can be created by consecutive pulsing pairs of electrodes positioned at different distances from the urethra along the same radius.

The treatment procedure with a urethra—perineal applicator starts by placing the probe 701 into the urethra 706. Balloon 705 at the distal end of the probe 703 is inflated. Inflated balloon 705 anchors the probe relatively to the urethra and the bladder. Due to selection of the location of electrode 708 on the probe 701, it can be positioned in the urethra at the exact location of the transition zone in the middle of the BPH overgrowth. As the probe 701 is being placed in the urethra, the needles 727 in cartridge 720 stay inactive, hidden in the back position. After the probe 701 is placed and anchored, the scrotum 715 is pulled aside and gently secured at a side and up position to avoid injury by the needles 727 to be advanced. Then the needles 727 are advanced into the forward position. They pierce the perineum 700 and the prostate 729 and deliver the needle electrodes 729 into the treatment positions around the central urethral electrode 708. After placement of all electrodes, the electroporation treatment is performed. Multiple high voltage pulses are delivered to the electrodes to create a radial to the urethra electric field to cause cell death and necrosis of a significant volume of neoplastic tissue, resulting in a relief of BPH symptoms. As the HV pulses are delivered the electrical resistance of the tissue is monitored. The end of the therapy is marked by a significant and stable drop in the resistance of the treated volume of tissue.

Placement of electrodes in the vicinity of prostate using a urethra-perineal applicator does not require ultrasound or other imaging guidance. Precise placement of the needles is provided by high mechanical tolerances of the applicator and high rigidity of the urethral probe. Using the urethra-perineal applicator allows for a short treatment time because it provides treatment in only one position of the electrodes, and does not require repositioning electrodes and multiple manipulation of the applicator.

The urethra-perineal applicator can be used for delivery of electrical energy to the prostate not only in the form of high voltage pulses causing electroporation necrosis, but also in the form of RF energy causing thermal necrosis of BPH.

Figure 9:
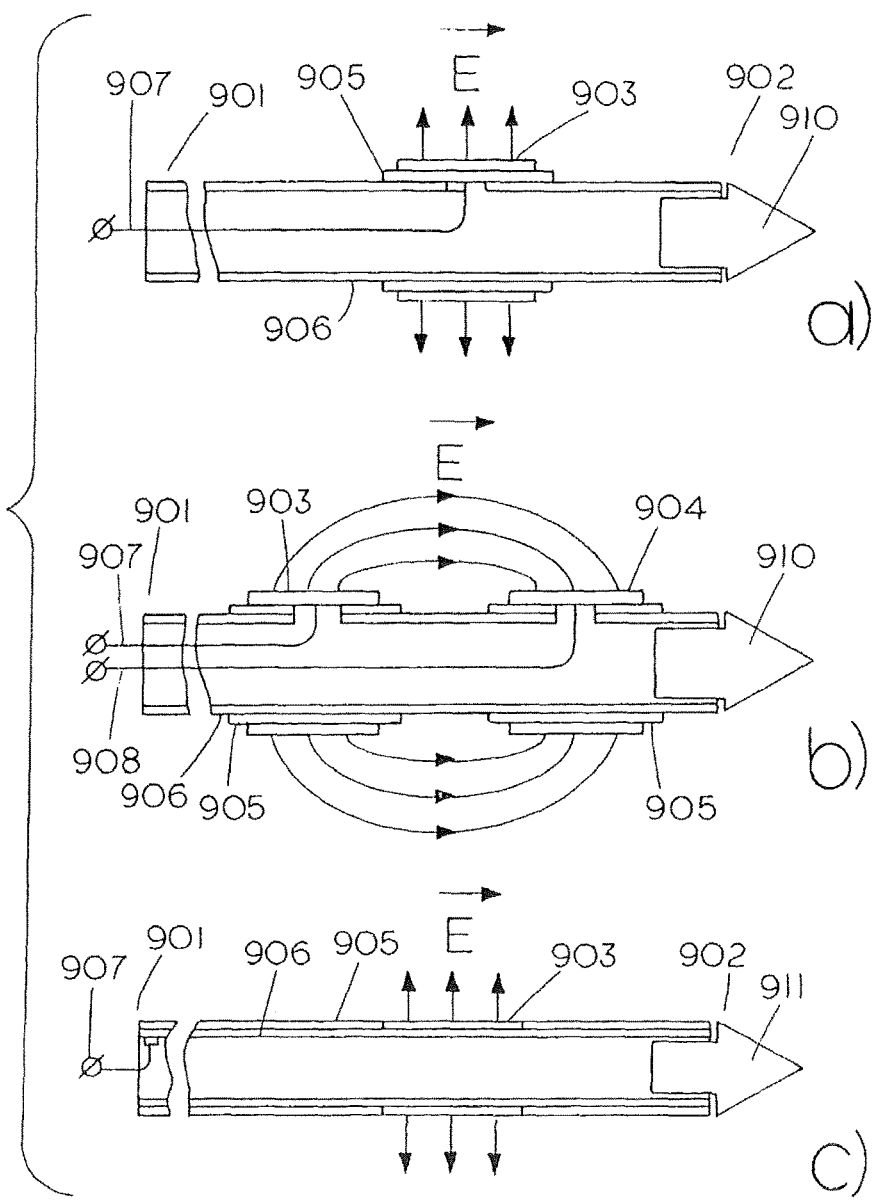

Different needle electrodes used in the electroporation treatment are shown in FIGS. 9a, b, c. FIG. 9a shows a one electrode needle adapted for creating electric field normal to the axis of the needle. The needle has a proximal end 901, distal end 902 and a metal hollow body 906. At the distal end 902 the needle is terminated by a sharp metal tip 910 (911), brazed into the hollow body of the needle. A cylindrical electrode 903 is secured on an insulator layer 905 deposited on the needle surface. The electrode 903 (904) is electrically connected to high voltage generator via a wire 907 (908). A version of a similar needle with two electrodes adapted for creating electric field directed along the axis of the needle is shown in the FIG. 9b.

In versions 9a and 9b the sharp tips are electrically separated from the HV electrodes. In version 9c the tip is made of an insulating material, like glass, dielectric crystal or ceramics. This feature of the design prevents electric breakdowns and sparking from the tip through the tissue during HV pulsing.

Although preferred embodiments of the invention have been described in some detail, it is understood that obvious variations can be made without departing from the spirit and the scope of the invention as defined by the appended claims.

What is claimed is:

1. A method for treating nerve cells around a tubular anatomical structure, the method comprising:
    advancing into the tubular anatomical structure a catheter having a balloon and at least one electrode;
    positioning the advanced electrode near a target area containing at least one nerve cell;
    expanding the balloon to place the at least one electrode near the target area;
    applying, using the positioned electrode, an electrical treatment signal in an amount sufficient to destroy the at least one nerve cell in the target area; wherein the electrical treatment signal has an amplitude of at least 1000 Volts/cm.

2. The method of claim 1, wherein the step of applying an electrical treatment signal includes applying a plurality of electrical signals in a direction substantially along the length of the at least one nerve cell.

3. The method of claim 1, wherein the electrical treatment signal is an amount above an upper limit of electroporation to irreversibly open pores in membranes of the at least one nerve cell, thereby killing the nerve cell.

4. The method of claim 1, wherein the electrical treatment signal has a duration of at least 10 microseconds.

5. The method of claim 1, wherein the at least one electrode comprises a plurality of electrodes and wherein the electrical treatment signal includes applying a plurality of rectangular electrical pulses to cause an electric field, wherein the plurality of electrical pulses is distributed among the plurality of electrodes through a switching circuit.

6. The method of claim 1, further comprising the step of cooling the tubular anatomical structure to a temperature in the range of 10 to 20 degrees Celsius.

7. The method of claim 1, wherein the step of applying includes applying the electrical current in a direction which is substantially radial to the tubular anatomical structure.

8. The method of claim 1, further comprising determining an endpoint by monitoring the resistance of the target area.

9. The method of claim 1, wherein the step of applying includes:
applying the electrical treatment signal in a direction substantially along the length of the at least one nerve cell and in a direction which is substantially radial to the tubular anatomical structure.

10. A method for treating nerve cells around a tubular anatomical structure, the method comprising:
advancing into the tubular anatomical structure a catheter having a balloon and at least one electrode;
positioning the advanced electrode near a target area containing at least one nerve cell;
expanding the balloon to place the at least one electrode near the target area;
preheating, using radio-frequency energy, the target area prior to applying an electrical treatment signal;
applying, using the positioned electrode, an electrical treatment signal in an amount sufficient to destroy the at least one nerve cell in the target area, wherein the electrical treatment signal includes applying a plurality of rectangular electrical pulses to cause an electric field, wherein the plurality of electrical pulses is distributed among the set of electrodes through a switching circuit; and wherein the electrical treatment signal has an amplitude of at least 1000 Volts/cm.

11. The method of claim 10, wherein the electrical treatment signal is an amount above an upper limit of electroporation to irreversibly open pores in membranes of the at least one nerve cell, thereby killing the nerve cell.

12. The method of claim 10, wherein the electrical treatment signal has a duration of at least 10 microseconds.

13. The method of claim 10, further comprising the step of determining an endpoint by monitoring the resistance of the target area.

14. A method for treating nerve cells around a tubular anatomical structure, the method comprising:
advancing into the tubular anatomical structure a catheter having a balloon and at least one electrode;
positioning the advanced electrode near a target area containing at least one nerve cell without piercing the target area;
expanding the balloon to place the at least one electrode near the target area;
applying, using the positioned electrode, an electrical treatment signal in an amount sufficient to destroy the at least one nerve cell in the target area; wherein the electrical treatment signal has an amplitude of at least 1000 Volts/cm; and
determining an endpoint by monitoring the resistance of the target area.

15. The method of claim 14, wherein the at least one electrode comprises a plurality of electrodes and wherein the electrical treatment signal includes applying a plurality of rectangular electrical pulses to cause an electric field, wherein the plurality of electrical pulses is distributed among the plurality of electrodes through a switching circuit.

16. The method of claim 14, wherein the electrical treatment signal is an amount above an upper limit of electroporation to irreversibly open pores in membranes of the at least one nerve cell, thereby killing the nerve cell.

17. The method of claim 14, wherein the electrical treatment signal has a duration of at least 10 microseconds.

* * * * *